United States Patent
Hayden et al.

(10) Patent No.: US 10,697,009 B2
(45) Date of Patent: *Jun. 30, 2020

(54) NUCLEOTIDE ANALOGS FOR SEQUENCING

(71) Applicant: IBIS BIOSCIENCES, INC., Carlsbad, CA (US)

(72) Inventors: Mark A. Hayden, Carlsbad, CA (US); Jeffrey Huff, Carlsbad, CA (US); Mark W. Eshoo, Carlsbad, CA (US); John Picuri, Carlsbad, CA (US)

(73) Assignee: IBIS BIOSCIENCES INC., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/538,278

(22) Filed: Aug. 12, 2019

(65) Prior Publication Data

US 2019/0367976 A1    Dec. 5, 2019

Related U.S. Application Data

(63) Continuation of application No. 14/775,067, filed as application No. PCT/US2014/024391 on Mar. 12, 2014, now Pat. No. 10,428,379.

(60) Provisional application No. 61/791,730, filed on Mar. 15, 2013.

(51) Int. Cl.
*C12Q 1/68* (2018.01)
*C07H 19/10* (2006.01)
*C07H 21/04* (2006.01)
*C12Q 1/6869* (2018.01)

(52) U.S. Cl.
CPC ........... *C12Q 1/6869* (2013.01); *C07H 19/10* (2013.01); *C07H 21/04* (2013.01)

(58) Field of Classification Search
CPC ............................ C12Q 1/6869; C07H 21/04
USPC ....................................... 536/4.1, 23.1, 26.6
See application file for complete search history.

(56) References Cited

U.S. PATENT DOCUMENTS

| | | |
|---|---|---|
| 4,889,818 A | 12/1989 | Gelfand et al. |
| 5,302,509 A | 4/1994 | Cheeseman |
| 5,374,553 A | 12/1994 | Gelfand et al. |
| 5,420,029 A | 5/1995 | Gelfand et al. |
| 5,455,170 A | 10/1995 | Abramson et al. |
| 5,466,591 A | 11/1995 | Abramson et al. |
| 5,618,711 A | 4/1997 | Gelfand et al. |
| 5,624,833 A | 4/1997 | Gelfand et al. |

(Continued)

FOREIGN PATENT DOCUMENTS

| | | |
|---|---|---|
| WO | WO-8909283 A1 | 10/1989 |
| WO | WO-9323564 A1 | 11/1993 |

(Continued)

OTHER PUBLICATIONS

Bashkin J.K., et al., "Sequence-Specific Cleavage of HIV mRNA by a Ribozyme Mimic," Journal of the American Chemical Society, 1994, vol. 116 (13), pp. 5981-5982.

(Continued)

*Primary Examiner* — Jezia Riley

(74) *Attorney, Agent, or Firm* — Casimir Jones S.C.; Kirk Hogan

(57) ABSTRACT

Provided herein is technology relating to sequencing nucleic acids, but not exclusively, to compositions, methods, systems, and kits related to nucleotides comprising an electrochemically detectable moiety and one or more photolabile synthesis-inhibiting moieties.

18 Claims, 1 Drawing Sheet

(56) References Cited

U.S. PATENT DOCUMENTS

| | | | |
|---|---|---|---|
| 5,674,738 | A | 10/1997 | Abramson et al. |
| 5,763,594 | A | 6/1998 | Hiatt et al. |
| 5,789,224 | A | 8/1998 | Gelfand et al. |
| 5,795,762 | A | 8/1998 | Abramson et al. |
| 5,808,045 | A | 9/1998 | Hiatt et al. |
| 5,872,244 | A | 2/1999 | Hiatt et al. |
| 5,939,292 | A | 8/1999 | Gelfand et al. |
| 6,057,096 | A | 5/2000 | Rothschild et al. |
| 6,214,987 | B1 | 4/2001 | Hiatt et al. |
| 6,232,465 | B1 | 5/2001 | Hiatt et al. |
| 6,329,178 | B1 | 12/2001 | Patel et al. |
| 6,395,524 | B2 | 5/2002 | Loeb et al. |
| 6,420,169 | B1 | 7/2002 | Read et al. |
| 6,602,695 | B2 | 8/2003 | Patel et al. |
| 6,833,246 | B2 | 12/2004 | Balasubramanian |
| 6,969,488 | B2 | 11/2005 | Bridgham et al. |
| 7,115,400 | B1 | 10/2006 | Adessi et al. |
| 7,170,050 | B2 | 1/2007 | Turner et al. |
| 7,476,503 | B2 | 1/2009 | Turner et al. |
| 7,486,865 | B2 | 2/2009 | Foquet et al. |
| 7,893,227 | B2 | 2/2011 | Wu et al. |
| 7,897,737 | B2 | 3/2011 | Wu et al. |
| 7,907,800 | B2 | 3/2011 | Foquet et al. |
| 7,923,562 | B2 | 4/2011 | Chen et al. |
| 7,932,034 | B2 | 4/2011 | Esfandyarpour et al. |
| 7,964,352 | B2 | 6/2011 | Wu et al. |
| 8,148,503 | B2 | 4/2012 | Litosh et al. |
| 8,153,375 | B2 | 4/2012 | Travers et al. |
| 8,361,727 | B2 | 1/2013 | Wu et al. |
| 8,501,405 | B2 | 8/2013 | Korlach et al. |
| 8,795,961 | B2 | 8/2014 | Rank et al. |
| 9,063,156 | B2 | 6/2015 | Korlach et al. |
| 2002/0012970 | A1 | 1/2002 | Smith et al. |
| 2003/0215862 | A1 | 11/2003 | Parce et al. |
| 2004/0005599 | A1 | 1/2004 | Schoenbrunner et al. |
| 2005/0037398 | A1 | 2/2005 | Gelfand et al. |
| 2005/0037991 | A1 | 2/2005 | Bodepudi et al. |
| 2007/0048748 | A1 | 3/2007 | Williams et al. |
| 2010/0035254 | A1 | 2/2010 | Williams |
| 2010/0048502 | A1 | 2/2010 | Dore et al. |
| 2010/0173303 | A1 | 7/2010 | Ronaghi et al. |
| 2011/0117637 | A1 | 5/2011 | Gray et al. |
| 2011/0270533 | A1 | 11/2011 | Zhang et al. |

FOREIGN PATENT DOCUMENTS

| | | | |
|---|---|---|---|
| WO | WO-2005040425 | A2 | 5/2005 |
| WO | WO-2007075967 | A2 | 7/2007 |
| WO | WO-2009152353 | A2 | 12/2009 |
| WO | WO-2013102081 | A2 | 7/2013 |

OTHER PUBLICATIONS

Braslavsky I., et al., "Sequence Information can be Obtained from Single DNA Molecules," Proceedings of the National Academy of Sciences, 2003, vol. 100 (7), pp. 3960-3964.

Efimov V.A., et al., "Synthesis of Polyacrylamides N-Substituted with Pna-Like Oligonucleotide Mimics for Molecular Diagnostic Applications," Nucleic Acids Research, 1999, vol. 27 (22), pp. 4416-4426.

Eid J., et al., "Real-time Dna Sequencing from Single Polymerase Molecules," Science, 2009, vol. 323 (5910), pp. 133-138.

Foquet M., et al., "Improved Fabrication of Zero-mode Waveguides for Single-molecule Detection," Journal of Applied Physics, 2008, vol. 103.

Gorodetsky A.A., et al., "Coupling into the Base Pair Stack is Necessary for DNA-Mediated Electrochemistry," Bioconjugate Chemistry, 2007, vol. 18 (5), pp. 1434-1441.

Guo J., et al., "Four-Color DNA Sequencing With 3'-O-Modified Nucleotide Reversible Terminators and Chemically Cleavable Fluorescent Dideoxynucleotides," Proceedings of theNational Academyof Sciences, 2008, vol. 105 (27), pp. 9145-9150.

Hall D.B., et al., "Sensitivity of DNA-Mediated Electron Transfer to the Intervening π-Stack: A Probe for the Integrity of the DNA Base Stack," Journal of the American Chemical Society, 1997, vol. 119 (21), pp. 5045-5046.

Hall D.B., et al., "Oxidative DNA Damage Through Long-Range Electron Transfer," Nature, 1996, vol. 382 (Nature), pp. 731-735.

Holmlin, R.E., et al., "Dipyridophenazine Complexes of Os(II) as Red-Emitting DNA Probes: Synthesis, Characterization, and Photophysical Properties," Inorganic Chemistry, 1999, vol. 38 (1), pp. 174-189.

Hurley D.J., et al., "Metal-Containing Oligonucleotides: Solid-Phase Synthesis and Luminescence Properties," Journal of the American Chemical Society, 1998, vol. 120 (9), pp. 2194-2195.

Hyman E.D., "A New Method of Sequencing DNA," Analytical Biochemistry, 1988, vol. 174 (2), pp. 423-436.

Ihara T., et al., "Ferrocene-Oligonucleotide Conjugates for Electrochemical Probing of DNA," Nucleic Acids Research, 1996, vol. 24 (21), pp. 4273-4280.

Ihara T., et al., "Gene Sensor using Ferrocenyl Oligonucleotide," Chemical Communications, 1997, vol. 17, pp. 1609-1610.

International Search Report and Written Opinion for Application No. PCT/US2014/024391, dated Jun. 17, 2014, 22 pages.

Ju J., et al., "Four-Color DNA Sequencing by Synthesis using Cleavable Fluorescent Nucleotide Reversible Terminators," Proceedings of the National Academy of Sciences, 2006, vol. 103 (52), pp. 19635-19640.

Korlach J., et al., "Selective Aluminum Passivation for Targeted Immobilization of Single DNA Polymerase Molecules in Zero-Mode Waveguide Nanostructures," Proceedings of the National Academy of Sciences, 2008, vol. 105 (4), pp. 1176-1181.

Korlach J., et al., "Long, Processive Enzymatic Dna Synthesis Using 100% Dye-labeled Terminal Phosphate-linked Nucleotides," Nucleosides Nucleotides Nucleic Acids, 2008, vol. 27 (9), pp. 1072-1083.

Lee H.B., et al., "Studies on a Dithiane-Protected Benzoin Photolabile Safety Catch Linker for Solid-Phase Synthesis," Journal of Organic Chemistry, 1999, vol. 64 (10), pp. 3454-3460.

Levene M.J., et al., "Zero-mode Waveguides for Single-molecule Analysis at High Concentrations," Science, 2003, vol. 299 (5607), pp. 682-686.

Litosh V.A., et al., "Improved Nucleotide Selectivity and Termination Of 3'-OH Unblocked Reversible Terminators by Molecular Tuning of 2-nitrobenzyl Alkylated HOMedU Triphosphates," Nucleic Acids Research, 2011, vol. 39 (6), p. e39.

Lundquist P.M., et al., "Parallel Confocal Detection of Single Molecules in Real Time," Optics Letters, 2008, vol. 33 (9), pp. 1026-1028.

MacLean D., et al., "Application of 'next-generation' Sequencing Technologies to Microbial Genetics," Nature Reviews Microbiology, 2009, vol. 7 (4), pp. 287-296.

Mead T.J., "Electron Transfer Through the DNA Double Helix," in: Metal Ions in Biological Systems, SIGEL.H., et al., Eds., Marcel Dekker: New York, 1995, vol. 32, pp. 453-478.

Meade T.J., et al., "Electron Transfer through DNA: Site-Specific Modification of Duplex DNA with Ruthenium Donors and Acceptors," Angewandte Chemie (International Edition in English), 1995, vol. 34 (3), pp. 352-354.

Meggers E., et al., "An Efficient Synthesis of Enantiomerically Pure Δ- and Λ-Ruthenium(II)-Labelled Oligonucleotides," Helvetica Chimica Acta, 1997, vol. 80 (3), pp. 640-652.

Mitra R.D., et al., "Fluorescent in Situ Sequencing on Polymerase Colonies," Analytical Biochemistry, 2003, vol. 320 (1), pp. 55-65.

Mucic R.C., et al., "Synthesis and Characterization of DNA with Ferrocenyl Groups Attached to their 5'-Termini: Electrochemical Characterization of a Redox-Active Nucleotide Monolayer," Chemical Communications, 1996, vol. 4, pp. 555-557.

Pike, et al., "Metallocene—DNA: Synthesis, Molecular and Electronic Structure and DNA Incorporation of C5-Ferrocenylthymidine Derivatives," Chemistry: A European Journal, 2002, vol. 8 (13), pp. 2891-2899.

Rack J.J., et al., "Spectroscopy and Electrochemistry of Ruthenium-Modified Nucleic Acids: Design of a Novel Metal-Binding Nucleoside," Journal of the American Chemical Society, 2000, vol. 122 (26), pp. 6287-6288.

(56) References Cited

OTHER PUBLICATIONS

Ronaghi M., et al., "A sequencing method based on real-time pyrophosphate," Science, 1998, vol. 281 (5375), pp. 363-365.

Ruparel H., et al., "Design and Synthesis of a 3'-o-allyl Photocleavable Fluorescent Nucleotide as a Reversible Terminator for Dna Sequencing by Synthesis," Proceedings of the National Academy of Sciences of the United States of America, 2005, vol. 102 (17), pp. 5932-5937.

Seo T.S., et al., "Four-color DNA Sequencing by Synthesis on a Chip Using Photocleavable Fluorescent Nucleotides," Proceedings of the National Academy of Sciences of the United States of America, 2005, vol. 102 (17), pp. 5926-5931.

Voelkerding K.V., et al., "Next-Generation Sequencing: from Basic Research to Diagnostics," Clinical Chemistry, 2009, vol. 55 (4), pp. 641-658.

Vrabel M., et al.,"Base-Modified DNA Labeled by [Ru(bpy)3]2+ and [Os(bpy)3]2+ Complexes: Construction by Polymerase Incorporation of Modified Nucleoside Triphosphates, Electrochemical and Luminescent Properties, and Applications," Chemistry: A European Journal, 2009, vol. 15 (5), pp. 1144-1154.

Yu, C.J., et al., "2'-Ribose-Ferrocene Oligonucleotides for Electronic Detection of Nucleic Acids," Journal of Organic Chemistry, 2001, vol. 66 (9), pp. 2937-2942.

Lee et al.,"DNA sequencing with dye-labeled terminators and T7 DNA polymerase: effect of dyes and dNTPs on incorporation of dye-terminators and probability analysis of termination fragments" Nucleic Acids Res. May 25, 1992:20(10):2471-83.

Supplementary European Search Report for Application No. EP14769128, dated Aug. 23, 2016, 8 pages.

Stratagene Catalog, p. 39, 1998.

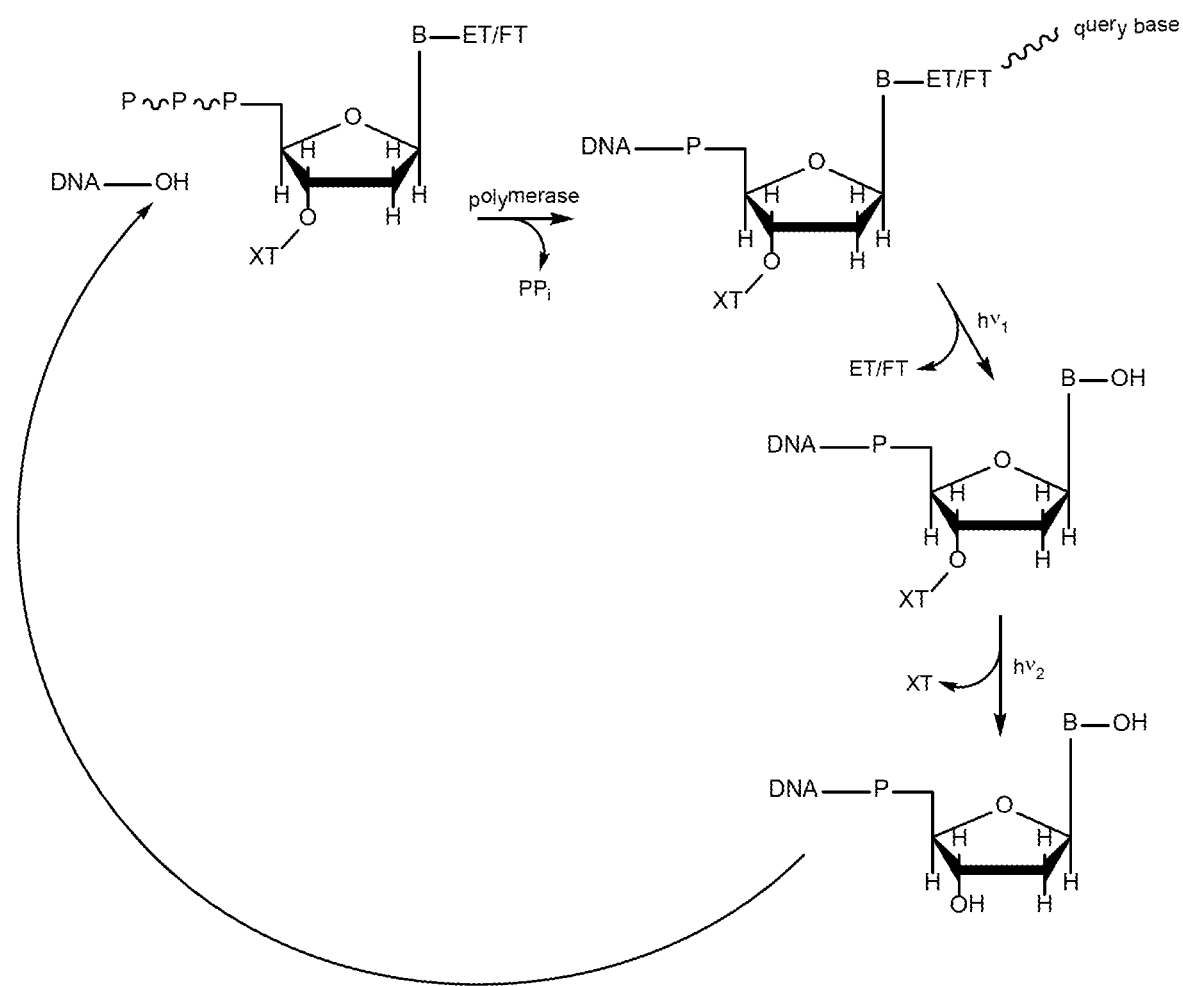

NUCLEOTIDE ANALOGS FOR SEQUENCING

This application is a continuation of U.S. patent application Ser. No. 14/775,067, filed Sep. 11, 2015, which is a 371 U.S. National Phase Entry of International Application No. PCT/US2014/024391, filed Mar. 12, 2014, which claims priority to U.S. provisional patent application Ser. No. 61/791,730, filed Mar. 15, 2013, which is incorporated herein by reference in its entirety.

FIELD OF INVENTION

Provided herein is technology relating to sequencing nucleic acids, but not exclusively, to compositions, methods, systems, and kits related to nucleotides comprising an electrochemically detectable moiety and one or more photolabile synthesis-inhibiting moieties.

BACKGROUND

DNA sequencing is driving genomics research and discovery. The completion of the Human Genome Project was a monumental achievement with incredible amount of combined efforts among genome centers and scientists worldwide. This decade-long project was completed using the Sanger sequencing method, which remains the staple genome sequencing methodology in high-throughput genome sequencing centers. The main reason behind the prolonged success of this method is its basic and efficient, yet elegant, method of dideoxy chain termination. With incremental improvements in Sanger sequencing—including the use of laser-induced fluorescent excitation of energy transfer dyes, engineered DNA polymerases, capillary electrophoresis, sample preparation, informatics, and sequence analysis software—the Sanger sequencing platform has been able to maintain its status. Current state-of-the-art Sanger based DNA sequencers can produce over 700 bases of clearly readable sequence in a single run from templates up to 30 kb in length. However, as it is with most technological inventions, the continual improvements in this sequencing platform has come to a stagnant plateau, with the current cost estimate for producing a high-quality microbial genome draft sequence at around $10,000 per megabase pair. Current DNA sequencers based on the Sanger method allow up to 384 samples to be analyzed in parallel.

It is evident that exploiting the complete human genome sequence for clinical medicine and health care requires accurate low-cost and high-throughput DNA sequencing methods. Indeed, both public (National Human Genome Research Institute, NHGRI) and private genomic sciences sector (The J. Craig Venter Science Foundation and Archon X prize for genomics) have issued a call for the development of "next-generation" sequencing technology that will reduce the cost of sequencing to one-ten thousandth of its current cost over the next ten years. Accordingly, to overcome the limitations of current conventional sequencing technologies, a variety of new DNA sequencing methods have been investigated, including sequencing-by-synthesis (SBS) approaches such as pyrosequencing (Ronaghi et al. (1998) Science 281: 363-365), sequencing of single DNA molecules (Braslaysky et al. (2003) Proc. Natl. Acad. Sci. USA 100: 3960-3964), and polymerase colonies ("polony" sequencing) (Mitra et al. (2003) Anal. Biochem. 320: 55-65).

Some conventional next-generation sequencing technologies include single molecule optical detection methods, e.g., as used in technologies developed by PacBio; optical (clonal) methods, e.g., as used in technologies developed by Illumina; and fluorescently labeled nucleotide based methods (including those that use photodeprotection), e.g., as used in technology developed by Lasergen. Such methods have varying degrees of advantages and disadvantages, but the significant challenge up until now has remained the issue of conducting such sequencing analyses with ultra-low cost instrumentation systems with truly low cost and disposable reagents.

The concept of DNA sequencing-by-synthesis (SBS) was revealed in 1988 with an attempt to sequence DNA by detecting the pyrophosphate group that is generated when a nucleotide is incorporated by a DNA polymerase reaction (Hyman (1999) Anal. Biochem. 174: 423-436). Subsequent SBS technologies were based on additional ways to detect the incorporation of a nucleotide to a growing DNA strand. In general, conventional SBS uses an oligonucleotide primer designed to anneal to a predetermined position of the sample template molecule to be sequenced. The primer-template complex is presented with a nucleotide in the presence of a polymerase enzyme. If the nucleotide is complementary to the position on the sample template molecule that is directly 3' of the end of the oligonucleotide primer, then the DNA polymerase will extend the primer with the nucleotide. The incorporation of the nucleotide and the identity of the inserted nucleotide can then be detected by, e.g., the emission of light, a change in fluorescence, a change in pH (see, e.g., U.S. Pat. No. 7,932,034), a change in enzyme conformation, or some other physical or chemical change in the reaction (see, e.g., WO 1993/023564 and WO 1989/009283; Seo et al. (2005) "Four-color DNA sequencing by synthesis on a chip using photocleavable fluorescent nucleotides," PNAS 102: 5926-59). Upon each successful incorporation of a nucleotide, a signal is detected that reflects the occurrence, identity, and number of nucleotide incorporations. Unincorporated nucleotides can then be removed (e.g., by chemical degradation or by washing) and the next position in the primer-template can be queried with another nucleotide species.

While it has become apparent that next-generation sequencing has broad application to diagnostics including cancer, infectious diseases, companion drugs, and hereditary diseases, the extant next-generation sequencing systems are designed to sequence whole genomes and therefore the systems a have high cost per test (e.g., approximately $100 to $500 per test). Moreover, implementing the current commercial systems is also expensive (e.g., $75,000 to $700,000) and the sample-to-sequence work flow is laborious. As such, the extant technologies do not provide a sample to sequence system that is desirable for diagnostic applications.

As such, it is a goal to generate high quality data at a reasonable cost and deliver next-generation sequencing data accurately and rapidly in an easy to use system. Companies such as PacBio have developed specific chemistries for implementation on their systems. At the same time, other companies such as VisiGen and Life Technologies have pursued alternative chemistries for addressing low cost sequencing.

In particular, LaserGen has developed approaches using optical detection systems and certain reaction chemistries to produce and polymerize photo-deprotectable nucleotides that could be employed in next generation sequencing applications, e.g., as described in U.S. Pat. Nos. 7,893,227; 7,897,737; 7,964,352; and 8,148,503. The LaserGen nucleotides have a photocleavable, fluorescent terminator moiety attached to the nucleotide base and a non-blocked 3' hydroxyl on the ribose sugar. The photocleavable, fluorescent terminator provides a substrate for polymerization, e.g., a polymerase adds the nucleotide analog to the 3' hydroxyl of the synthesized strand. While attached to the nucleotide at the 3' end, the photocleavable, fluorescent terminator prevents additional nucleotide addition by the polymerase. Also, the fluorescent moiety provides for identification of the nucleotide added using an excitation light source and a fluorescence emission detector. Upon exposure to a light source of the appropriate wavelength, the light cleaves the photocleavable, fluorescent terminator from the 3' end of the strand, thus removing the block to synthesis and another nucleotide analog is added to begin the cycle again. When used in a sequencing-by-synthesis reaction, the LaserGen fluorescently labeled nucleotide compounds offer a way to photodeprotect and at the same time allow for extension, e.g., by sterically unblocking the region in the enzyme so as to permit extension. However, these compounds suffer from having to use fluorescence to detect the presence or absence of a particular incorporation event. As such, the need to use optical detection in the context of utilizing optical cleavage of photodeprotectible labels in these technologies is prohibitive to achieving the lowest optimal cost in creating a low-cost sequencing system. The system requires careful coordination of the excitation and deprotecting light sources so that excitation does not deprotect free or incorporated nucleotides. Accordingly, extant methods and previous ideas are inadequate for achieving the desired optimal cost for sequencing.

SUMMARY

Accordingly, provided herein is technology for sequencing nucleic acids that uses an optical deprotection chemistry to control step-wise sequencing of a nucleic acid strand and an electrochemical means for detecting and identifying each particular base. One advantage of the technology is that the cost and complexity of the optical detection components in a sequencer are reduced while maintaining the advantageous use of photochemical deprotection as the fundamental approach to controlling the sequencing reaction. Consequently, the technologies described herein afford a lower cost for sequencing than conventional technologies that rely on both photochemical deprotection and optical detection.

In one aspect, technology is provided herein that comprises use of an electrical detection element in conjunction with photo-activated deprotection of nucleotide analogs. In addition, the technology implements these components into a zero mode waveguide approach to next-generation sequencing. Combining electrical deprotection with electrical detection allows sequencing systems to implement global illumination, rather than optical scanning, to deprotect massively parallel sequencing reactions. In addition, using an electrical detector in lieu of costly ultrahigh resolution scanning elements that find use in conventional, extant optical detection systems reduces the complexity and cost of the optics bench. As a result, detection speed is increased and the cost per read is decreased.

The technology finds use in sequencing-by-synthesis methods, e.g., as provided by the Solexa/Illumina platform (see, e.g., Voelkerding et al., *Clinical Chem.* 55: 641-658, 2009; MacLean et al., *Nature Rev. Microbiol.* 7: 287-296; and in U.S. Pat. Nos. 6,833,246; 7,115,400; and 6,969,488; each incorporated by reference herein in its entirety).

Furthermore, the use of the zero mode waveguide approach, e.g., stochastic/optical confinement of single molecules, and optically deblockable nucleotides enables next-generation sequencing-by-synthesis methods using a single sequencing fluid rather than a series of inefficient wash steps. Conventional next-generation sequencing-by-synthesis requires washing the reaction after each base addition. These washes increase sequencing time and the cost of sequencing by necessitating more complex fluidics and large volumes of expensive reagents. As provided by the technology herein, the optically deblockable, electrochemically detectable nucleotides are used in a zero mode wave guide sequencing system, which enables deblocking the nucleotide at the site of the extending polymerase (in the illumination volume of the zero-mode waveguide) without deblocking the other nucleotides in the reaction mixture. As a result, a single fluid is used without requiring washing the reaction mixture after each base addition. In some embodiments, the detection of the incorporated nucleotides is by electrochemical means rather than by optical means.

In one aspect, the technology provides classes of chemical structures (e.g., nucleotide analogs) that improve the accuracy of sequencing. In some embodiments, the nucleotide analogs are synthesized using existing chemistry approaches modified to include an electrochemical, rather than a fluorescent, detection element. In some embodiments, the technology provides nucleotide analogs for electrochemical detection and photochemical deprotection.

In some embodiments, the technology relates to a new chemical class of photo-deprotectable nucleotide analogs that comprise an electrochemically detectable terminating moiety on the nucleotide base. In some embodiments, the technology relates to a new chemical class of photo-deprotectable nucleotide analogs that comprise an electrochemically detectable terminating moiety on the nucleotide 3' end. In some embodiments, the technology is related to a new chemical class of photo-deprotectable nucleotide analogs that comprise an electrochemically or fluorescently detectable terminating moiety on the nucleotide base and a terminating moiety on the nucleotide 3' end. As such, related aspects provide a technology for sequencing by sequentially removing the electrochemically or fluorescently detectable terminating moiety from the nucleotide base and removing the terminating moiety from the nucleotide 3' end, e.g., by exposure to a light source or sources that provide a light (e.g., a photon or more than one photon) that cleaves the terminating moieties from the nucleotide analog. Unlike conventional technologies, embodiments of the technology provide a nucleotide that is de-blocked with light to permit extension of the nucleic acid polymer by a nucleic acid polymerase and detection of the nucleotide is by electrochemical means rather than by optical means.

For example, in some embodiments sequencing is performed by the following sequence of events with the exemplary use of a nucleotide comprising at least two different photochemical terminating moieties. First, a nucleotide analog comprising an electrochemically or fluorescently detectable terminating moiety (e.g., attached to the nucleotide base) and a second terminating moiety (e.g., attached to the 3' hydroxyl) is oriented in the polymerase active site (e.g., by a polymerase located in the illumination volume of a zero mode waveguide) to be base-paired to a complementary base of the template strand and to be adjacent to the free 3' hydroxyl of the growing synthesized strand. Next, the nucleotide analog is added to the 3' end of a growing strand by the polymerase, e.g., by the enzyme-catalyzed attack of the 3' hydroxyl on the alpha-phosphate of the nucleotide analog. Further extension of the strand by the polymerase is blocked by the 3' terminating group on the incorporated nucleotide analog. The electrochemically or fluorescently detectable moiety on the incorporated nucleotide is queried by an electrochemical detector or by a fluorescence detector (e.g., after excitation by an emission source) to identify the base added to the synthesized strand.

Then, the electrochemically or fluorescently detectable terminating moiety (e.g., attached to the nucleotide base) is removed by exposure (e.g., in the illumination volume of a zero mode waveguide) to a wavelength of light that cleaves the electrochemically or fluorescently detectable terminating moiety from the nucleotide analog. While the electrochemically or fluorescently detectable terminating moiety has been released, further extension of the strand by the polymerase remains blocked by the 3' terminating group (second terminating moiety) on the incorporated nucleotide analog. Then, the second terminating moiety is removed by exposure (e.g., in the illumination volume of a zero mode waveguide) to a wavelength of light that cleaves the second terminating moiety from the nucleotide analog. In some embodiments, the wavelength of light that cleaves the electrochemically or fluorescently detectable terminating moiety is different than the wavelength of light that cleaves the second terminating moiety, e.g., blocking the 3' hydroxyl. After the second terminating moiety is released, the 3' hydroxyl of the growing strand is free for further polymerization: the next base is incorporated to continue another cycle, e.g., a nucleotide analog is oriented in the polymerase active site, the nucleotide analog is added to the 3' end of the growing strand by the polymerase, the nucleotide analog is queried to identify the base added, and the nucleotide analog is deprotected.

In some embodiments sequencing is performed by the following sequence of events with the exemplary use of a nucleotide comprising one photochemical terminating moiety. First, a nucleotide analog comprising an electrochemically detectable terminating moiety (e.g., attached to the nucleotide base) is oriented in the polymerase active site (e.g., by a polymerase located in the illumination volume of a zero mode waveguide) to be base-paired to a complementary base of the template strand and to be adjacent to the free 3' hydroxyl of the growing synthesized strand. Next, the nucleotide analog is added to the 3' end of a growing strand by the polymerase, e.g., by the enzyme-catalyzed attack of the 3' hydroxyl on the alpha-phosphate of the nucleotide analog. Further extension of the strand by the polymerase is blocked by the electrochemically detectable terminating moiety of incorporated nucleotide analog, e.g., by steric hindrance of the catalysis, deformation of the active site constituents, etc. The electrochemically detectable moiety on the incorporated nucleotide is queried by an electrochemical detector to identify the base added to the synthesized strand.

Then, the electrochemically detectable terminating moiety (e.g., attached to the nucleotide base) is removed by exposure (e.g., in the illumination volume of a zero mode waveguide) to a wavelength of light that cleaves the electrochemically detectable terminating moiety from the nucleotide analog. After the electrochemically detectable terminating moiety is released, the 3' hydroxyl of the growing strand is free for further polymerization: the next base is incorporated to continue another cycle, e.g., a nucleotide analog is oriented in the polymerase active site, the nucleotide analog is added to the 3' end of the growing strand by the polymerase, the nucleotide analog is queried to identify the base added, and the nucleotide analog is deprotected.

Accordingly, in some embodiments, the technology provides that nucleotides on the end of the chain are 3' protected so they cannot react with the 5' triphosphate from new nucleotides coming into the active site until after deblocking the 3' end (either by removing a terminating moiety from the 3' hydroxyl or by removing steric hindrance to polymerization). Thus, one can read all or substantially all of the fluorescence or electrochemical signal without the problems associated with reincorporation and reading of the next base. In embodiments related to electrochemical detection based reagents, such reagents are developed for sequencing using photochemical deprotection using a single photochemical deprotection group and an electrochemically active element serving for detection. This approach improves existing technologies (e.g., as provided by the LaserGen chemistry) and thus finds use in sequencing by synthesis applications having increased accuracy and lower cost by including these approaches on low cost optical systems such as zero mode waveguide-based systems and the like.

Accordingly, provided herein is technology related to a nucleotide analog comprising a nucleotide comprising a phosphate moiety, a base, and a sugar; and an electrochemically detectable, photocleavable terminating moiety attached to the nucleotide. In some embodiments, the nucleotide analog comprises an electrochemically detectable, photocleavable terminating moiety that is attached to the phosphate moiety of the nucleotide. In some embodiments, the nucleotide analog comprises an electrochemically detectable, photocleavable terminating moiety that is attached to the base of the nucleotide. In some embodiments, the nucleotide analog comprises an electrochemically detectable, photocleavable terminating moiety that is attached to the sugar of the nucleotide.

Embodiments provide that the photocleavable terminating moieties are photocleavable, e.g., they are cleavable from the nucleotide analog upon exposure to a light source of the appropriate wavelength and intensity to effect cleavage. As such, in some embodiments the nucleotide analog comprises an electrochemically detectable, photocleavable terminating moiety that is attached to the nucleotide by a photocleavable linker. In some embodiments, the electrochemically detectable, photocleavable terminating moiety has a structure that is:

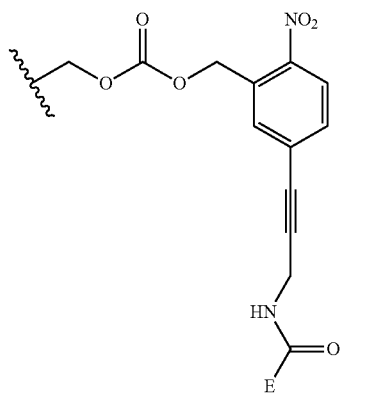

or

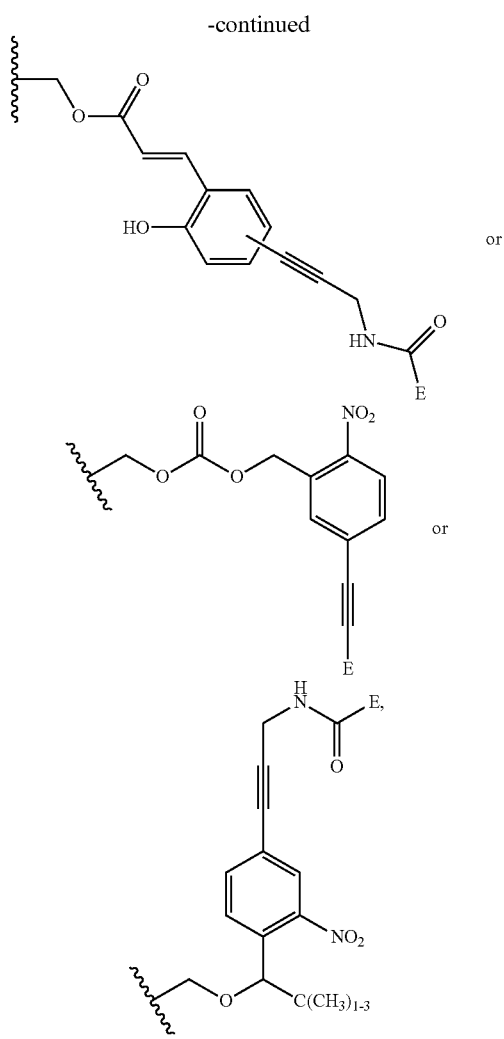

where E represents an electrochemically detectable moiety or label, e.g., an electrochemical tag that is an easily oxidizable or reducible species such as an organic redox group, an organometallic group, a metallic nanoparticle, and a quantum dot. Exemplary organic redox groups include, but are not limited to, methylene blue, anthraquinone, and thionine; exemplary organometallic groups include, but are not limited to, ferrocene, ferrocene derivatives, bipyridene complexes of ruthenium, and bipyridene complexes of osmium; exemplary metallic nanoparticles include, but are not limited to, gold and silver; exemplary quantum dots include, but are not limited to, CdS, CdSe, and ZnS. In some embodiments, it is contemplated that the nucleotide analogs comprise a structure as provided in U.S. Pat. Nos. 7,893,227; 7,897,737; 7,964,352; and 8,148,503, with the fluorescent moiety described therein replaced by an electrochemically detectable moiety as described herein or as known in the art.

In some embodiments, the nucleotide analog comprises an electrochemically detectable, photocleavable terminating moiety that is attached to the nucleotide by a photocleavable linker selected from the group consisting of ether, ester, diester, etc. The present technology encompasses, in some embodiments, photocleavable linkers including, but not limited to, 2-nitrobenzyl moieties, alpha-substituted 2-nitrobenzyl moieties (e.g. 1-(2-nitrophenyl)ethyl moieties), 3,5-dimethoxybenzyl moieties, thiohydroxamic acid, 7-nitroindoline moieties, 9-phenylxanthyl moieties, benzoin moieties, hydroxyphenacyl moieties, and N-hydroxy-succinimidyl-4-azidosalicylic acid (NHS-ASA) moieties. The present technology also contemplates photocleavable linkers comprising 2-nitrobenzyl moieties and "cross-linker arms" (or "spacer arms") that further separate a photocleavable linker from a nucleotide to which it is to be operably linked. Examples of such "cross-linker arms" include, but are not limited to, long alkyl chains or repeat units of caproyl moieties linked via amide linkages.

In some embodiments, the nucleotide analog comprises a second photocleavable terminating moiety attached to the nucleotide, e.g., attached to the sugar of the nucleotide, e.g., at the 3' position of the sugar. Exemplary photocleavable terminating moieties that find use as a second photocleavable terminating moiety attached to the nucleotide include, but are not limited to

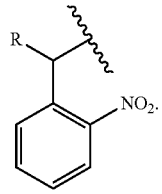

The technology is not limited in the moiety used to block the 3' end. For example, a method of sequencing using 3'-O-allyl modified nucleotide analogs is described in Ruparel et al. (2005) Proc. Natl. Acad. Sci. 102: 5932-5937. Other reversible terminators are described, e.g., in U.S. Pat. Nos. 5,872,244; 6,232,465; 6,214,987; 5,808,045; 5,763,594, and 5,302,509; and U.S. Patent Application Publication No. 20030215862. In some embodiments, a 2'-modified (e.g., 2'-phosphate) nucleoside 5' triphosphate finds use in the technology, e.g., as has been described as a substrate for certain nucleic acid polymerizing enzymes (see, e.g., U.S. Patent Application Publication Nos. 2005/00373898 and 2005/0037991). Other 3' blockers are provided in, e.g., Guo et al. (2008) "Four-color DNA Sequencing with 3'-O-modified Nucleotide Reversible Terminators and Chemically Cleavable Fluorescent Dideoxynucleotides" Proc Nat'l Acad Sci USA 105: 9145-9150 and in Ju et al (2006) "Four-Color DNA Sequencing by Synthesis Using Cleavable Fluorescent Nucleotide Reversible Terminators" Proc Nat'l Acad Sci USA 103: 19635-19640.

In some embodiments, the nucleotide analog further comprises a second photocleavable terminating moiety attached to the nucleotide, wherein the second photocleavable terminating moiety is attached to the nucleotide by a photocleavable linker. In some embodiments, the nucleotide analog further comprises a second photocleavable terminating moiety attached to the nucleotide, wherein the second photocleavable terminating moiety is attached to the nucleotide by a photocleavable linker. In some embodiments the nucleotide analog further comprises a second photocleavable terminating moiety attached to the nucleotide, wherein the second photocleavable terminating moiety is attached to the nucleotide by a photocleavable linker that is different than the photocleavable linker attached to the electrochemically detectable, photocleavable terminating moiety.

The technology is not limited in the photocleavable linkers used to attach a detectable moiety (e.g., an electrochemically and/or a fluorescently detectable moiety). For instance, the present technology encompasses photocleavable linkers including, but not limited to, 2-nitrobenzyl moieties, alpha-substituted 2-nitrobenzyl moieties (e.g. 1-(2-nitrophenyl)ethyl moieties), 3,5-dimethoxybenzyl moieties, thiohydroxamic acid, 7-nitroindoline moieties, 9-phenylxanthyl moieties, benzoin moieties, hydroxyphenacyl moieties, and N-hydroxy-succinimidyl-4-azidosalicylic acid (NHS-ASA) moieties. The present technology also contemplates photocleavable linkers comprising 2-nitrobenzyl moieties and "cross-linker arms" (or "spacer arms") that further separate a photocleavable linker from a nucleotide to which it is to be operably linked. Examples of such "cross-linker arms" include, but are not limited to, long alkyl chains or repeat units of caproyl moieties linked via amide linkages.

It is preferable that the light required to activate cleavage does not affect the other components of the modified nucleotides. For example, if a fluorophore is used as the label, it is preferable if this absorbs light of a different wavelength to that required to cleave the linker molecule. Suitable linkers include those based on O-nitrobenzyl compounds and nitroveratryl compounds. Linkers based on benzoin chemistry can also be used. See, e.g., Lee et al. (1999) *J. Org. Chem.* 64: 3454-3460, incorporated herein by reference.

Provided herein are nucleotide analogs comprising a nucleotide (e.g., comprising a phosphate moiety, a base, and a sugar); an electrochemically detectable, photocleavable terminating moiety attached to the base of the nucleotide; and a second photocleavable terminating moiety attached to the sugar of the nucleotide. Moreover, also provided are nucleotide analogs comprising a nucleotide (e.g., comprising a phosphate moiety, a base, and a sugar); a fluorescently detectable, photocleavable terminating moiety attached to the nucleotide; and a second photocleavable terminating moiety attached to the nucleotide.

In some embodiments of the nucleotide analog the fluorescently detectable, photocleavable terminating moiety is attached the phosphate moiety of the nucleotide and the second photocleavable terminating moiety is attached to the sugar of the nucleotide. In some embodiments of the nucleotide analog of claim the fluorescently detectable, photocleavable terminating moiety is attached the base of the nucleotide and the second photocleavable terminating moiety is attached to the sugar of the nucleotide.

The technology is not limited in the fluorescent moieties and/or photocleavable groups that are attached to the nucleotide analogs. For instance, in some embodiments of the nucleotide analog the fluorescently detectable, photocleavable terminating moiety comprises a fluorescently detectable moiety that is based on a dye, wherein the dye is xanthene, fluorescein, rhodamine, BODIPY, cyanine, coumarin, pyrene, phthalocyanine, phycobiliprotein, ALEXA FLUOR® 350, ALEXA FLUOR® 405, ALEXA FLUOR® 430, ALEXA FLUOR® 488, ALEXA FLUOR® 514, ALEXA FLUOR® 532, ALEXA FLUOR® 546, ALEXA FLUOR® 555, ALEXA FLUOR® 568, ALEXA FLUOR® 568, ALEXA FLUOR® 594, ALEXA FLUOR® 610, ALEXA FLUOR® 633, ALEXA FLUOR® 647, ALEXA FLUOR® 660, ALEXA FLUOR® 680, ALEXA FLUOR® 700, ALEXA FLUOR® 750, or a squaraine dye; and the second photocleavable terminating moiety is

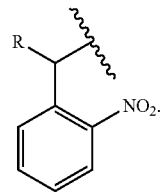

In some embodiments, the fluorescently detectable, photocleavable terminating moiety is attached to the nucleotide by a first photocleavable linker and the second photocleavable terminating moiety is attached to the nucleotide by a second photocleavable linker. In some embodiments are provided a nucleotide analog comprising a nucleotide (e.g., comprising a phosphate moiety, a base, and a sugar); a fluorescently detectable, photocleavable terminating moiety attached to the base of the nucleotide; and a second photocleavable terminating moiety attached to the sugar of the nucleotide.

The technology encompasses natural and synthetic nucleotides and bases. As such, in some embodiments the nucleotide analog comprises a nucleotide that is adenine, cytosine, guanine, thymine, or uracil. In some embodiments, the nucleotide comprises a phosphate moiety that is a triphosphate, a diphosphate, or a monophosphate.

The technology relates to nucleotides that find use in sequencing-by-synthesis. Accordingly, embodiments of nucleotides comprise a photocleavable terminating moiety that is a group imparting polymerase termination properties to the nucleotide analog.

Related embodiments provide compositions that comprise a nucleotide analog and a polymerase. The technology is not limited in the polymerase that finds use in the technology. Polymerases that find use include, but are not limited to, Taq DNA polymerase, Klenow (exo⁻) DNA polymerase, Bst DNA polymerase, VENT® (exo⁻) DNA polymerase (e.g., a DNA polymerase A cloned from *Thermococcus litoralis* and containing the D141A and E143A mutations), Pfu (exo⁻) DNA polymerase, and DEEPVENT™ (exo⁻) DNA polymerase (DNA polymerase A cloned from the *Pyrococcus* species GB-D and containing the D141A and E143A mutations), AMPLITAQ® DNA polymerase, FS (Taq DNA polymerase that contains the G46D and F667Y mutations), THERMOSEQUENASE™ DNA polymerase (Taq DNA polymerase that contains the F667Y mutation), THERMOSEQUENASE™ II DNA polymerase (blend of THERMOSEQUENASE™ DNA polymerase and *T. acidophilum* pyrophosphatase), THERMINATOR™ DNA polymerase (DNA polymerase A cloned from the *Thermococcus* species 9°N-7 and containing the D141A, E143A, and A485L mutations), THERMINATOR™ II DNA polymerase (THERMINATOR™ DNA polymerase that contains the additional Y409V mutation), and VENT® (exo⁻) A488L DNA polymerase (VENT® (exo⁻) DNA polymerase that contains the A488L mutation). In some embodiments are provided a composition that further comprises a nucleic acid, e.g., a template that is to be sequenced (e.g., to have its nucleotide sequence determined).

In some embodiments, a polymerase is modified to enhance incorporation of the nucleotide analogs disclosed herein. Exemplary modified polymerases are disclosed in U.S. Pat. Nos. 4,889,818; 5,374,553; 5,420,029; 5,455,170; 5,466,591; 5,618,711; 5,624,833; 5,674,738; 5,789,224; 5,795,762; 5,939,292; and U.S. Patent Publication Nos. 2002/0012970 and 2004/0005599. A non-limiting example of a modified polymerase includes G46E E678G CS5 DNA polymerase, G46E E678G CS5 DNA polymerase, E615G Taq DNA polymerase, ΔZO5R polymerase, and G46E L329A E678G CS5 DNA polymerase disclosed in U.S. Patent Publication No. 2005/0037398. The production of modified polymerases can be accomplished using many conventional techniques in molecular biology and recombinant DNA described herein and known in the art. In some embodiments, wherein the 2'-phosphate unblocking generates a 2'-hydroxyl, e.g., a ribonucleotide, polymerase mutants, such as those described in U.S. Pat. No. 5,939,292, which incorporate NTPs as well as dNTPs can be used.

Furthermore, the technology provides embodiments of methods for sequencing a nucleic acid, the methods comprising hybridizing a primer to a nucleic acid to form a hybridized primer/nucleic acid complex; providing a plurality of nucleotide analogs, the nucleotide analogs comprising a nucleotide and an electrochemically detectable, photocleavable terminating moiety attached to the nucleotide; reacting the hybridized primer/nucleic acid complex and the nucleotide analog with a polymerase to add the nucleotide analog to the primer by a polymerase reaction to form an extended product comprising an incorporated nucleotide analog; querying the extended product to identify the incorporated nucleotide analog; and exposing the extended product to a light source providing a wavelength of light to remove an electrochemically detectable, photocleavable terminating moiety from the incorporated nucleotide analog. In some embodiments, the methods comprise use of a nucleotide analog that further comprises a second photocleavable terminating moiety attached to the nucleotide and the method further comprises exposing the extended product to a light source providing a second wavelength of light to remove a second photocleavable terminating moiety from the incorporated nucleotide analog.

Exemplary embodiments for sequencing a nucleic acid comprise hybridizing a primer to a nucleic acid to form a hybridized primer/nucleic acid complex; providing a plurality of nucleotide analogs, each nucleotide analog comprising a nucleotide and a fluorescently detectable, photocleavable terminating moiety attached to the nucleotide and a second photocleavable terminating moiety attached to the nucleotide; reacting the hybridized primer/nucleic acid complex and the nucleotide analog with a polymerase to add the nucleotide analog to the primer by a polymerase reaction to form an extended product comprising an incorporated nucleotide analog; querying the extended product to identify the incorporated nucleotide analog; exposing the extended product to a light source providing a first wavelength of light to remove a fluorescently detectable, photocleavable terminating moiety from the incorporated nucleotide analog; and exposing the extended product to a light source providing a second wavelength of light to remove a second photocleavable terminating moiety from the incorporated nucleotide analog.

Embodiments of the methods provide for determining the sequence of multiple bases (nucleotides) of a nucleic acid. Accordingly, embodiments are provided wherein the method further comprises repeating the reacting, querying, and exposing steps one or more additional cycles to identify a plurality of bases in the nucleic acid, wherein the reacting step of cycle n+1 comprises reacting the extended product of cycle n and a nucleotide analog with the polymerase to add the nucleotide analog to the extended product of cycle n by a polymerase reaction to form an extended product of cycle n+1 comprising an incorporated nucleotide analog.

Some embodiments provide for the use of zero mode waveguide in a sequencing method. As such, in some embodiments the methods further provide a substrate comprising a zero mode waveguide and locating the polymerase within an observation volume of the zero mode waveguide. The nucleotide analogs provide for the identification of a nucleotide by the fluorescently detectable or electrically detectable moiety attached to the nucleotide analog. Accordingly, the technology provides in some embodiments that the querying step is performed with an electrical detection element, e.g., comprising use of cyclic voltammetry, adsorption stripping voltammetry, alternating current voltammetry, differential pulse voltammetry, and chemiluminescence. In some embodiments, querying is performed by a fluorescence detection element, e.g., by exposing a fluorescent moiety to an emission wavelength from a light source and detecting an emission from the fluorescent moiety. In some embodiments, exposing the extended product to the first wavelength of light is simultaneous to exposing the extended product to the second wavelength of light; in some embodiments, exposing the extended product to the first wavelength of light is before or after exposing the extended product to the second wavelength of light.

In some embodiments, the technology provides nucleotide analogs comprising two photocleavable moieties and related embodiments of methods wherein exposing the extended product to the first wavelength of light does not remove the second photocleavable terminating moiety from the incorporated nucleotide analog and exposing the extended product to the second wavelength of light does not remove the electrochemically detectable, photocleavable terminating moiety or the fluorescently detectable, photocleavable terminating from the nucleotide analog.

Some photocleavable groups are cleaved by exposure to one photon of light at the appropriate wavelength and some photocleavable groups are cleaved by exposure to two or more photons of light. As such, in some embodiments, exposing the extended product to a light source providing a first wavelength of light to remove an electrochemically detectable, photocleavable terminating moiety or a fluorescently detectable, photocleavable terminating moiety from the incorporated nucleotide analog comprises exposing the extended product to one photon of the first wavelength and exposing the extended product to a light source providing a second wavelength of light to remove a second photocleavable terminating moiety from the incorporated nucleotide analog comprises exposing the extended product to more than one photon of the second wavelength; alternatively, some embodiments provide that exposing the extended product to a light source providing a first wavelength of light to remove an electrochemically detectable, photocleavable terminating moiety or a fluorescently detectable, photocleavable terminating moiety from the incorporated nucleotide analog comprises exposing the extended product to more than one photon of the first wavelength and exposing the extended product to a light source providing a second wavelength of light to remove a second photocleavable terminating moiety from the incorporated nucleotide analog comprises exposing the extended product to one photon of the second wavelength.

Some embodiments provide that the wavelength of light used to cleave a photocleavable terminating moiety is 354 nm, 766 nm, or 520 nm. Sequencing methods as provided herein incorporate natural and synthetic analogs of nucleotides; e.g., embodiments provide that the nucleotide is adenine, cytosine, guanine, thymine, or uracil. The methods are related to sequencing-by-synthesis methods, e.g., methods comprising use of a photocleavable terminating moiety that is a group imparting polymerase termination properties to the nucleotide analog and the method comprises inhibiting a reacting step when an incorporated nucleotide comprises a photocleavable terminating moiety.

Accordingly, the technology also provides compositions for sequencing a nucleic acid. For example, embodiments provide a composition for sequencing a nucleic acid comprising four nucleotide analogs as described herein, wherein a first nucleotide analog comprises an adenine nucleotide, a second nucleotide analog comprises a cytosine nucleotide, a third nucleotide analog comprises a guanine nucleotide, and a fourth nucleotide analog comprises a thymine or a uracil nucleotide. The electrochemically or fluorescently detectable moiety attached to the nucleotides is used to identify the nucleotide that is incorporated into a nucleic acid during a sequencing-by-synthesis reaction. Thus, the technology is related to a composition for sequencing a nucleic acid, the composition comprising four nucleotide analogs as described herein, wherein a first nucleotide analog comprises a first electrochemically detectable moiety or a first fluorescently detectable moiety, a second nucleotide analog comprises a second electrochemically detectable moiety or a second fluorescently detectable moiety, a third nucleotide analog comprises a third electrochemically detectable moiety or a third fluorescently detectable moiety, and a fourth nucleotide analog comprises a fourth electrochemically detectable moiety or a fourth fluorescently detectable moiety.

Also described herein are kit embodiments of the technology. As such, kit embodiments for sequencing a nucleic acid comprise four nucleotide analogs as described herein, wherein a first nucleotide analog comprises an adenine nucleotide, a second nucleotide analog comprises a cytosine nucleotide, a third nucleotide analog comprises a guanine nucleotide, and a fourth nucleotide analog comprises a thymine or a uracil nucleotide. Additional kit embodiments for sequencing a nucleic acid comprise four nucleotide analogs as described herein, wherein a first nucleotide analog comprises a first electrochemically detectable moiety or a first fluorescently detectable moiety, a second nucleotide analog comprises a second electrochemically detectable moiety or a second fluorescently detectable moiety, a third nucleotide analog comprises a third electrochemically detectable moiety or a third fluorescently detectable moiety, and a fourth nucleotide analog comprises a fourth electrochemically detectable moiety or a fourth fluorescently detectable moiety. Some embodiments of kits comprise four nucleotide analogs as described herein, wherein a first nucleotide analog comprises an adenine nucleotide, a second nucleotide analog comprises a cytosine nucleotide, a third nucleotide analog comprises a guanine nucleotide, and a fourth nucleotide analog comprises a thymine or a uracil nucleotide; and a polymerase. Furthermore, some kit embodiments comprise four nucleotide analogs as described herein, wherein a first nucleotide analog comprises a first electrochemically detectable moiety or a first fluorescently detectable moiety, a second nucleotide analog comprises a second electrochemically detectable moiety or a second fluorescently detectable moiety, a third nucleotide analog comprises a third electrochemically detectable moiety or a third fluorescently detectable moiety, and a fourth nucleotide analog comprises a fourth electrochemically detectable moiety or a fourth fluorescently detectable moiety; and a polymerase.

Systems for sequencing a nucleic acid are also encompassed by the technology provided herein. In some embodiments, the technology provides a system for sequencing a nucleic acid, the system comprising a nucleotide analog as described herein, a composition as described herein, or a kit as described herein; one or more coherent light sources; and a fluorescence or electrochemical detection element. System embodiments further comprise one or more of a polymerase, a zero mode waveguide, a computer to identify bases and collect sequence information, and/or a software component to acquire and analyze sequence data.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 1 is a diagram showing a method embodiment of the technology provided herein. The drawing shows the polymerization of a nucleotide analog to the hydroxyl (—OH) of a DNA strand; the identification of the incorporated base ("query base") via its electrochemically detectable or fluorescently detectable moiety; photocleavage of a electrochemically detectable terminator moiety or a fluorescently detectable terminator moiety (ET/FT) by a first wavelength of light ($hv_1$); photocleavage of a second terminator moiety (XT) by a second wavelength of light ($hv_2$); which provides a free hydroxyl group on the growing DNA strand for the cycle to repeat with the next nucleotide analog to be incorporated.

It is to be understood that the FIGURES are not necessarily drawn to scale, nor are the objects in the FIGURES necessarily drawn to scale in relationship to one another. The FIGURES are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology relating to sequencing nucleic acids, but not exclusively, to compositions, methods, systems, and kits related to nucleotides comprising an electrochemically detectable moiety and one or more photolabile synthesis-inhibiting moieties.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

DEFINITIONS

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, a "nucleotide" comprises a "base" (alternatively, a "nucleobase" or "nitrogenous base"), a "sugar" (in particular, a five-carbon sugar, e.g., ribose or 2-deoxyribose), and a "phosphate moiety" of one or more phosphate groups (e.g., a monophosphate, a diphosphate, or a triphosphate consisting of one, two, or three linked phosphates, respectively). Without the phosphate moiety, the nucleobase and the sugar compose a "nucleoside". A nucleotide can thus also be called a nucleoside monophosphate or a nucleoside diphosphate or a nucleoside triphosphate, depending on the number of phosphate groups attached. The phosphate moiety is usually attached to the 5-carbon of the sugar, though some nucleotides comprise phosphate moieties attached to the 2-carbon or the 3-carbon of the sugar. Nucleotides contain either a purine (in the nucleotides adenine and guanine) or a pyrimidine base (in the nucleotides cytosine, thymine, and uracil). Ribonucleotides are nucleotides in which the sugar is ribose. Deoxyribonucleotides are nucleotides in which the sugar is deoxyribose.

As used herein, a "nucleic acid" shall mean any nucleic acid molecule, including, without limitation, DNA, RNA, and hybrids thereof. The nucleic acid bases that form nucleic acid molecules can be the bases A, C, G, T and U, as well as derivatives thereof. Derivatives of these bases are well known in the art. The term should be understood to include, as equivalents, analogs of either DNA or RNA made from nucleotide analogs. The term as used herein also encompasses cDNA, that is complementary, or copy, DNA produced from an RNA template, for example by the action of a reverse transcriptase. It is well known that DNA (deoxyribonucleic acid) is a chain of nucleotides consisting of 4 types of nucleotides—A (adenine), T (thymine), C (cytosine), and G (guanine)—and that RNA (ribonucleic acid) is a chain of nucleotides consisting of 4 types of nucleotides—A, U (uracil), G, and C. It is also known that all of these 5 types of nucleotides specifically bind to one another in combinations called complementary base pairing. That is, adenine (A) pairs with thymine (T) (in the case of RNA, however, adenine (A) pairs with uracil (U)), and cytosine (C) pairs with guanine (G), so that each of these base pairs forms a double strand. As used herein, "nucleic acid sequencing data", "nucleic acid sequencing information", "nucleic acid sequence", "genomic sequence", "genetic sequence", "fragment sequence", or "nucleic acid sequencing read" denotes any information or data that is indicative of the order of the nucleotide bases (e.g., adenine, guanine, cytosine, and thymine/uracil) in a molecule (e.g., a whole genome, a whole transcriptome, an exome, oligonucleotide, polynucleotide, fragment, etc.) of DNA or RNA It is well known that DNA (deoxyribonucleic acid) is a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. It is also known that all of these 5 types of nucleotides specifically bind to one another in combinations called complementary base pairing. That is, adenine (A) pairs with thymine (T) (in the case of RNA, however, adenine (A) pairs with uracil (U)), and cytosine (C) pairs with guanine (G), so that each of these base pairs forms a double strand. As used herein, "nucleic acid sequencing data," "nucleic acid sequencing information," "nucleic acid sequence," "genomic sequence," "genetic sequence," or "fragment sequence," or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

Reference to a base, a nucleotide, or to another molecule may be in the singular or plural. That is, "a base" may refer to a single molecule of that base or to a plurality of the base, e.g., in a solution.

A "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

As used herein, the phrase "dNTP" means deoxynucleotidetriphosphate, where the nucleotide comprises a nucleotide base, such as A, T, C, G or U.

The term "monomer" as used herein means any compound that can be incorporated into a growing molecular chain by a given polymerase. Such monomers include, without limitations, naturally occurring nucleotides (e.g., ATP, GTP, TTP, UTP, CTP, dATP, dGTP, dTTP, dUTP, dCTP, synthetic analogs), precursors for each nucleotide, non-naturally occurring nucleotides and their precursors or any other molecule that can be incorporated into a growing polymer chain by a given polymerase.

As used herein, "complementary" generally refers to specific nucleotide duplexing to form canonical Watson-Crick base pairs, as is understood by those skilled in the art. However, complementary also includes base-pairing of nucleotide analogs that are capable of universal base-pairing with A, T, G or C nucleotides and locked nucleic acids that enhance the thermal stability of duplexes. One skilled in the art will recognize that hybridization stringency is a determinant in the degree of match or mismatch in the duplex formed by hybridization.

As used herein, "moiety" refers to one of two or more parts into which something may be divided, such as, for example, the various parts of a tether, a molecule or a probe.

The phrase "electrochemically detectable moiety", as used herein, refers to a substance that can accept or donate at least one electron during an electrochemical reaction, typically oxidation and/or reduction (redox). Each electrochemical event, namely an electron transfer to or from the electrochemically detectable moiety, contributes to an electrical current or voltage that the system can sense and record.

As used herein, a "linker" is a molecule or moiety that joins two molecules or moieties and provides spacing between the two molecules or moieties such that they are able to function in their intended manner. For example, a linker can comprise a diamine hydrocarbon chain that is covalently bound through a reactive group on one end to an oligonucleotide analog molecule and through a reactive group on another end to a solid support, such as, for example, a bead surface. Coupling of linkers to nucleotides and substrate constructs of interest can be accomplished through the use of coupling reagents that are known in the art (see, e.g., Efimov et al., Nucleic Acids Res. 27: 4416-4426, 1999). Methods of derivatizing and coupling organic molecules are well known in the arts of organic and bioorganic chemistry. A linker may also be cleavable (e.g., photocleavable) or reversible.

As used herein, the term "photocleavable linker" refers to a linker that may be removed from a nucleotide, polynucleotide, chemical group, or nucleic acid, to which it is attached or operably linked, by exposure to electromagnetic radiation (e.g., visible light, ultraviolet light, etc.). The wavelength of light used to photocleave the linker is dependent upon the structure of the photocleavable linker used.

A "polymerase" is an enzyme generally for joining 3'-OH 5'-triphosphate nucleotides, oligomers, and their analogs. Polymerases include, but are not limited to, DNA-dependent DNA polymerases, DNA-dependent RNA polymerases, RNA-dependent DNA polymerases, RNA-dependent RNA polymerases, T7 DNA polymerase, T3 DNA polymerase, T4 DNA polymerase, T7 RNA polymerase, T3 RNA polymerase, SP6 RNA polymerase, DNA polymerase 1, Klenow fragment, *Thermophilus aquaticus* DNA polymerase, Tth DNA polymerase, Vent DNA polymerase (New England Biolabs), Deep Vent DNA polymerase (New England Biolabs), Bst DNA Polymerase Large Fragment, Stoeffel Fragment, 9° N DNA Polymerase, Pfu DNA Polymerase, Tfl DNA Polymerase, RepliPHI Phi29 Polymerase, Tli DNA polymerase, eukaryotic DNA polymerase beta, telomerase, Therminator polymerase (New England Biolabs), KOD HiFi. DNA polymerase (Novagen), KOD1 DNA polymerase, Q-beta replicase, terminal transferase, AMV reverse transcriptase, M-MLV reverse transcriptase, Phi6 reverse transcriptase, HIV-1 reverse transcriptase, novel polymerases discovered by bioprospecting, and polymerases cited in U.S. Pat. Appl. Pub. No. 2007/0048748 and in U.S. Pat. Nos. 6,329,178; 6,602,695; and 6,395,524. These polymerases include wild-type, mutant isoforms, and genetically engineered variants such as exo– polymerases and other mutants, e.g., that tolerate labeled nucleotides and incorporate them into a strand of nucleic acid.

The term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, a "system" denotes a set of components, real or abstract, comprising a whole where each component interacts with or is related to at least one other component within the whole.

Various nucleic acid sequencing platforms, nucleic acid assembly and/or mapping systems (e.g., computer software and/or hardware) are described, e.g., in U.S. Pat. Appl. Pub. No. 2011/0270533, which is incorporated herein by reference.

As used herein, the terms "alkyl" and the prefix "alk-" are inclusive of both straight chain and branched chain saturated or unsaturated groups, and of cyclic groups, e.g., cycloalkyl and cycloalkenyl groups. Unless otherwise specified, acyclic alkyl groups are from 1 to 6 carbons. Cyclic groups can be monocyclic or polycyclic and preferably have from 3 to 8 ring carbon atoms. Exemplary cyclic groups include cyclopropyl, cyclopentyl, cyclohexyl, and adamantyl groups. Alkyl groups may be substituted with one or more substituents or unsubstituted. Exemplary substituents include alkoxy, aryloxy, sulfhydryl, alkylthio, arylthio, halogen, alkylsilyl, hydroxyl, fluoroalkyl, perfluoroalkyl, amino, aminoalkyl, disubstituted amino, quaternary amino, hydroxyalkyl, carboxyalkyl, and carboxyl groups. When the prefix "alk" is used, the number of carbons contained in the alkyl chain is given by the range that directly precedes this term, with the number of carbons contained in the remainder of the group that includes this prefix defined elsewhere herein. For example, the term "$C_1$-$C_4$ alkaryl" exemplifies an aryl group of from 6 to 18 carbons (e.g., see below) attached to an alkyl group of from 1 to 4 carbons.

As used herein, the term "aryl" refers to a carbocyclic aromatic ring or ring system. Unless otherwise specified, aryl groups are from 6 to 18 carbons. Examples of aryl groups include phenyl, naphthyl, biphenyl, fluorenyl, and indenyl groups.

As used herein, the term "heteroaryl" refers to an aromatic ring or ring system that contains at least one ring heteroatom (e.g., O, S, Se, N, or P). Unless otherwise specified, heteroaryl groups are from 1 to 9 carbons. Heteroaryl groups include furanyl, thienyl, pyrrolyl, imidazolyl, pyrazolyl, oxazolyl, isoxazolyl, thiazolyl, isothiazolyl, triazolyl, tetrazolyl, oxadiazolyl, oxatriazolyl, pyridyl, pyridazyl, pyrimidyl, pyrazyl, triazyl, benzofuranyl, isobenzofuranyl, benzothienyl, indole, indazolyl, indolizinyl, benzisoxazolyl, quinolinyl, isoquinolinyl, cinnolinyl, quinazolinyl, napthyridinyl, phthalazinyl, phenanthrolinyl, purinyl, and carbazolyl groups.

As used herein, the term "heterocycle" refers to a non-aromatic ring or ring system that contains at least one ring heteroatom (e.g., O, S, Se, N, or P). Unless otherwise specified, heterocyclic groups are from 2 to 9 carbons. Heterocyclic groups include, for example, dihydropyrrolyl, tetrahydropyrrolyl, piperazinyl, pyranyl, dihydropyranyl, tetrahydropyranyl, dihydrofuranyl, tetrahydrofuranyl, dihydrothiophene, tetrahydrothiophene, and morpholinyl groups.

Aryl, heteroaryl, or heterocyclic groups may be unsubstituted or substituted by one or more substituents selected from the group consisting of $C_{1-6}$ alkyl, hydroxy, halo, nitro, $C_{1-6}$ alkoxy, $C_{1-6}$ alkylthio, trifluoromethyl, $C_{1-6}$ acyl, arylcarbonyl, heteroarylcarbonyl, nitrile, $C_{1-6}$ alkoxycarbonyl, alkaryl (where the alkyl group has from 1 to 4 carbon atoms), and alkheteroaryl (where the alkyl group has from 1 to 4 carbon atoms).

As used herein, the term "alkoxy" refers to a chemical substituent of the formula —OR, where R is an alkyl group. By "aryloxy" is meant a chemical substituent of the formula —OR', where R' is an aryl group.

As used herein, the term "$C_{x-y}$ alkaryl" refers to a chemical substituent of formula —RR', where R is an alkyl group of x toy carbons and R' is an aryl group as defined elsewhere herein.

As used herein, the term "$C_{x-y}$ alkheteraryl" refers to a chemical substituent of formula RR", where R is an alkyl group of x to y carbons and R" is a heteroaryl group as defined elsewhere herein.

As used herein, the term "non-vicinal O, S, or N" refers to an oxygen, sulfur, or nitrogen heteroatom substituent in a linkage, where the heteroatom substituent does not form a bond to a saturated carbon that is bonded to another heteroatom.

Embodiments of the Technology

The technology described herein relates to nucleotide analogs and related methods, compositions (e.g., reaction mixtures), kits, and systems for sequencing nucleic acids. In particular, some embodiments of the nucleotide analogs comprise a photocleavable terminator to control step-wise sequencing of a nucleic acid strand and an electrochemically detectable moiety for the detection and identification of each particular base, e.g., to determine a nucleic acid sequence. The technology provides advantages over conventional methods such as a lower cost and reduced complexity.

Nucleotide Analogs

Provided herein are analogs of nucleotides. The nucleotide analogs comprise one or more photocleavable terminator moieties, e.g., that further comprise, in some embodiments, a fluorescently detectable moiety or an electrochemically detectable moiety. For example, the technology provides a nucleotide such as:

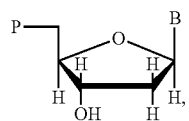

wherein P is the phosphate moiety (e.g., a monophosphate, a diphosphate, or a triphosphate) as defined herein and B is a base, e.g., adenine, thymine, cytosine, guanine, or uracil.

The nucleotide analogs are not limited to a specific phosphate group. In one embodiments, the phosphate group is a monophosphate group or a polyphosphate such as a diphosphate group or a triphosphate group. In some embodiments, the phosphate group is a pyrophosphate. Moreover, the base of the nucleotide analogs is not limited to a specific base. In some embodiments, the base is an adenine, cytosine, guanine, thymine, uracil, and analogs thereof such as, for example, acyclic bases. The nucleotide analogs are not limited to a specific sugar moiety. In some embodiments, said sugar moiety is a ribose, deoxyribose, dideoxyribose, and analogs thereof.

In some embodiments, the nucleotide analog has a structure that is:

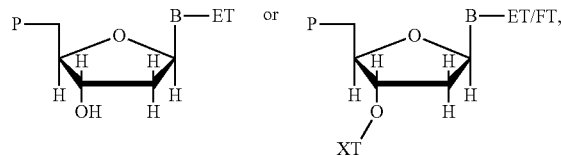

wherein ET is an electrochemically detectable terminator moiety (e.g., comprising an electrochemically detectable moiety E as described herein or as is known in the art), ET/FT is a fluorescently detectable terminator moiety (e.g., comprising a fluorescently detectable moiety as described herein, e.g., "F" in structures provided herein) or an electrochemically detectable terminator moiety (e.g., comprising an electrochemically detectable moiety as described herein, e.g., "E" in structures provided herein, or as is known in the art), and XT is a second terminating moiety (e.g., as provided herein and/or as known in the art). In some embodiments are provided four nucleotide analogs each comprising a different ET or FT and comprising the same XT.

For example, in some embodiments ET is

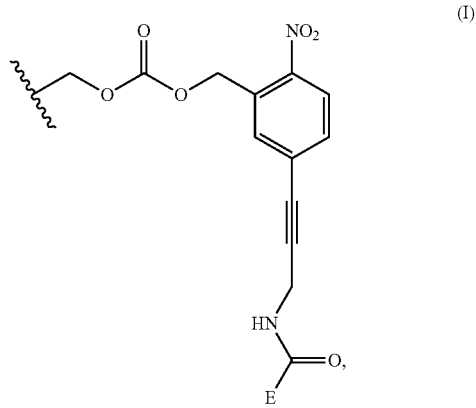

-continued

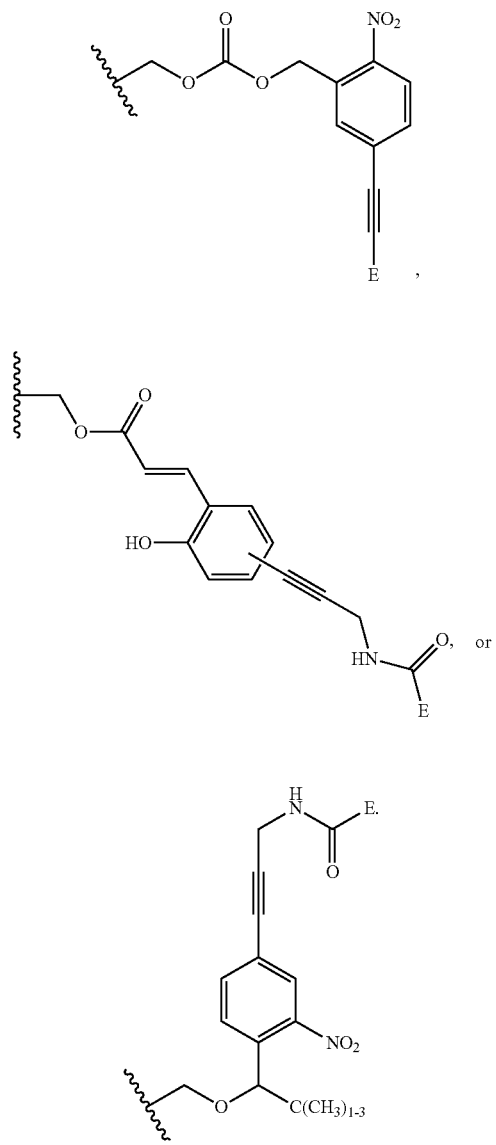

In some embodiments, FT is

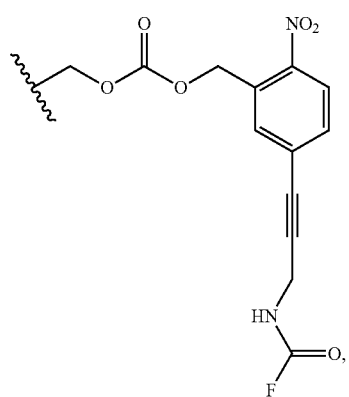

In some embodiments, XT is

The synthesis of compounds provide herein is performed as described, e.g., in U.S. Pat. Nos. 7,893,227; 7,897,737; 7,964,352; and 8,148,503, with the modifications as needed to replace fluorescent moieties with electrochemically detectable moieties to provide the various nucleotide analogs described herein. Additional synthetic schemes are provided in the example below.

In some embodiments, the terminators III and VII are cleaved by a photon of light having a wavelength of 500-550 nm (e.g., 520 nm). In some embodiments, the terminator XT is cleaved by a photon of light having a wavelength of 325-375 nm (e.g., 354 nm). In some embodiments, the terminators II and VI are cleaved by photons of light (e.g., two or more photons) having a wavelength of 740-780 nm (e.g., 766 nm). Examples of the products of cleavage are:
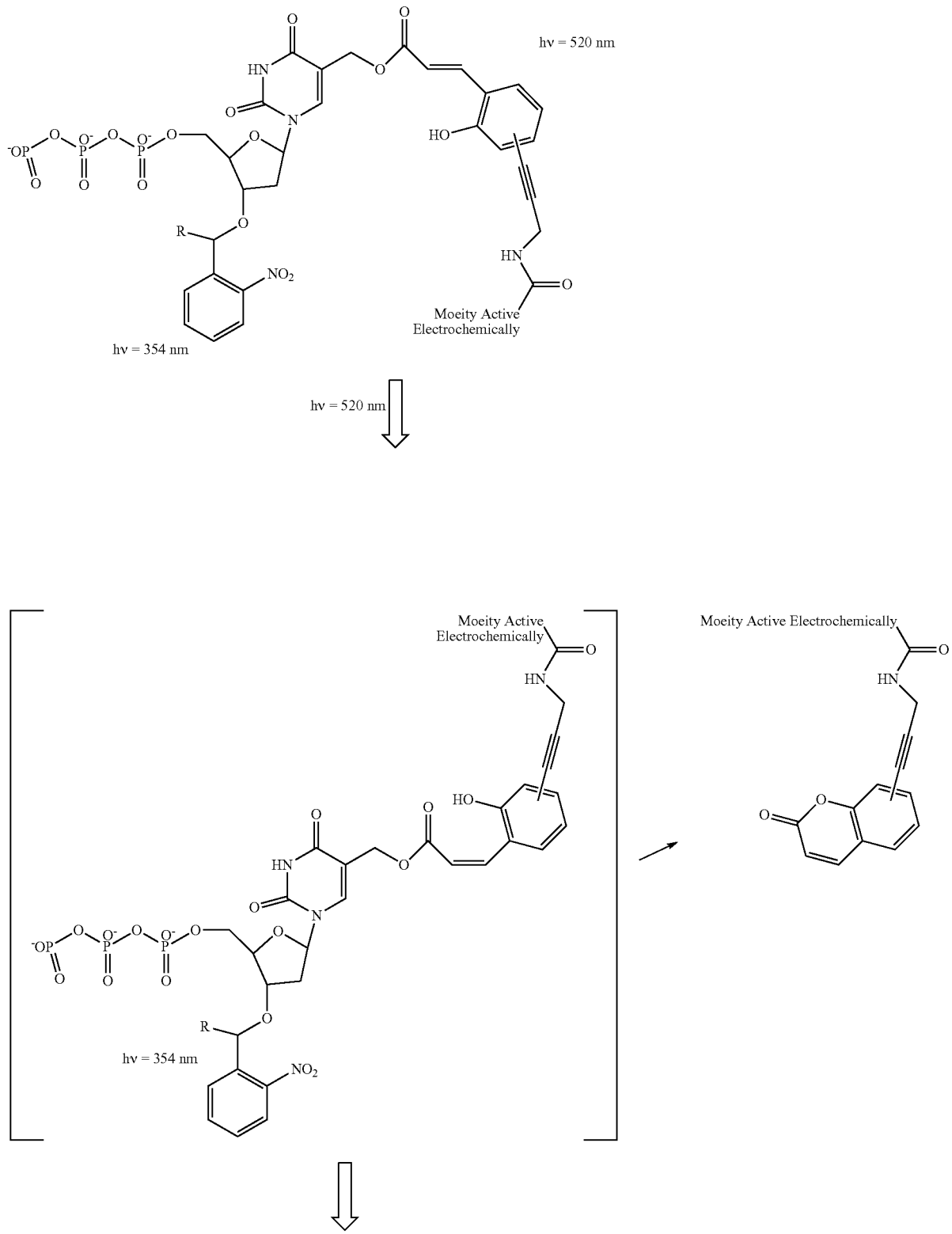

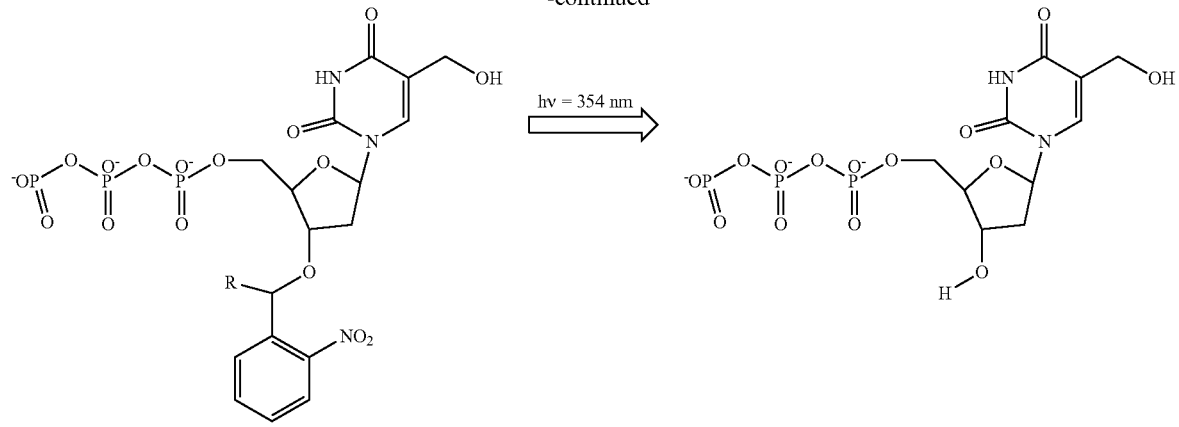

In some embodiments, the technology allows one to deprotect the 3' end and the base selectively and/or sequentially in the same system by fine tuning the wavelengths used to deprotect, e.g., so that one bond can be broken by one color of light before the other bond is broken by the other color of light. The color of light is used as a specific "switch" break the bonds (e.g., to release the terminators) but without impacting or damaging the un-intended bond. This allows control and affords various benefits described herein. In some embodiments, the nucleotide analogs comprise an electrical detection element, e.g., as embodied by the new compounds provided herein and for improved compounds comprising a fluorescent label in conventional use. The improved compounds eliminate or minimize the undesirable fluorescent features and associated maladies suffered by that prior art.

In this scheme above, once the electrochemical moiety has been queried to identify the base that was incorporated, it is removed from the base using photocleavage and it diffuses away from the location of the sequencing reaction (e.g., a sequencing reaction in a stochastically confined space such as in a zero mode wave guide or similar nanostructure). The growing chain is free to begin the cycle again and identify the next base in the sequence.

In similar embodiments, a nucleotide analog such as those described in, e.g., U.S. Pat. Nos. 7,893,227; 7,897,737; 7,964,352; and 8,148,503, and in Litosh et al (2010) "Improved nucleotide selectivity and termination of 3'-OH unblocked reversible terminators by molecular tuning of 2-nitrobenzyl alkylated HOMedU triphosphates" *Nucleic Acids Res.* 39(6):e39, and others, are modified (e.g., a terminator nucleotide analog in which a fluorescently detectable moiety is replaced by an electrochemically detectable moiety) and used without the dual photochemical labeled approach. Accordingly, it is to be understood that the technology also provides an improvement of existing nucleotide analogs such as photochemical deprotectible compounds in general and is not limited to use in the dual wavelength mode as described above.

Zero Mode Waveguides

In some assays, molecules are confined in a series, array, or other arrangement of small holes, pores, or wells, for example, a zero mode waveguide (ZMW), e.g., as described in U.S. Pat. Appl. Pub. No. 2011/0117637, incorporated herein by reference. ZMW arrays have been applied to a range of biochemical analyses and have found particular usefulness for genetic analysis. ZMWs typically comprise a nanoscale core, well, or opening disposed in an opaque cladding layer that is disposed upon a transparent substrate, e.g., a circular hole in an aluminum cladding film deposited on a clear silica substrate. See, e.g., J. Korlach et al, "Selective aluminum passivation for targeted immobilization of single DNA polymerase molecules in zero-mode waveguide nanostructures", 105 *PNAS* 1176-81 (2008). A typical ZMW hole is ~70 nm in diameter and ~100 nm in depth. ZMW technology allows the sensitive analysis of single molecules because, as light travels through a small aperture, the optical field decays exponentially inside the chamber. That is, due to the narrow dimensions of the well, electromagnetic radiation that is of a frequency above a particular cut-off frequency will be prevented from propagating all the way through the core. Notwithstanding the foregoing, the radiation will penetrate a limited distance into the core, providing a very small illuminated volume within the core. By illuminating a very small volume, one can interrogate very small quantities of reagents, including, e.g., single molecule reactions. The observation volume within an illuminated ZMW is ~20 zeptoliters ($20 \times 10^{-21}$ liters). Within this volume, the activity of DNA polymerase incorporating a single nucleotide can be readily detected.

By monitoring reactions at the single molecule level, one can precisely identify and/or monitor a given reaction. In particular, in some embodiments zero mode waveguide technology is the basis for a field of single molecule DNA sequencing that monitors the molecule-by-molecule (e.g., nucleotide-by-nucleotide) synthesis of a DNA strand in a template-dependent fashion by a single polymerase enzyme (e.g., Single Molecule Real Time (SMRT) DNA Sequencing as performed, e.g., by a Pacific Biosciences RS Sequencer (Pacific Biosciences, Menlo Park, Calif.)). See, e.g., U.S. Pat. Nos. 7,476,503; 7,486,865; 7,907,800; and 7,170,050; and U.S. patent application Ser. Nos. 12/553,478, 12/767,673; 12/814,075; 12/413,258; and Ser. No. 12/413,466, each incorporated herein by reference in its entirety for all purposes. See also, Eid, J. et al. 2009. "Real-time DNA sequencing from single polymerase molecules", 323 Science: 133-38 (2009); Korlach, J. et al. "Long, processive enzymatic DNA synthesis using 100% dye-labeled terminal phosphate-linked nucleotides", 27 Nucleosides, Nucleotides & Nucleic Acids: 1072-82 (2008); Lundquist, P. M. et al., "Parallel confocal detection of single molecules in real time", 33 Optics Letters: 1026-28 (2008); Korlach, J. et al., "Selective aluminum passivation for targeted immobilization of single dna polymerase molecules in zero-mode waveguide nanostructures", 105 Proc Natl Acad Sci USA: 1176-81 (2008); Foquet, M. et al., "Improved fabrication of zero-mode waveguides for single-molecule detection", 103 Journal of Applied Physics (2008); and Levene, M. J. et al. "Zero-mode waveguides for single-molecule analysis at high concentrations", 299 Science: 682-86 (2003), each incorporated herein by reference in its entirety for all purposes.

In some technologies, placing components in the wells of the ZMW relies on simple diffusion to deliver components (e.g., macromolecules such as DNA polymerase and/or DNA and/or DNA/DNA polymerase complexes) to the desired site (e.g., the bottom of the ZMW well) in the zero mode waveguides. Some technologies place components in the wells of a ZMW using technology based on the active transport of assay components (e.g., a macromolecule such as a DNA, a DNA polymerase, a DNA/DNA polymerase complex, a protein, etc.) to a desired site for an assay (e.g., the bottom of a ZMW well). Particular variations of active transport and delivery technologies use actin filaments or microtubules that are bound to the bottom of a zero mode waveguide. The actin filaments or microtubules serve as transport guides for the macromolecules (e.g., the DNA polymerase or DNA polymerase/DNA complex). See, e.g., U.S. Provisional Application Ser. No. 61/581,508 filed Dec. 29, 2011, and International Application Number PCT/US12/72075, each incorporated herein by reference.

In certain embodiments, the technology finds use for DNA sequencing methods using zero-mode waveguides (ZMWs), e.g., as developed by Pacific Biosciences or similar methods. In some embodiments of this technology, DNA sequencing is performed on a chip, each containing thousands of zero-mode waveguides (ZMWs). In some embodiments, a ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters ($10^{-21}$ L). At this volume, the activity of a single molecule can be detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Nucleotide analogs as provided herein, each type (e.g., A, T, C, and G) labeled with a different colored fluorophore or different electrochemically detectable group, are then introduced into the reaction solution at high concentrations that promote enzyme speed, accuracy, and processivity. Due to the small size of the ZMW, even at these high, biologically relevant concentrations, the detection volume is occupied by nucleotides only a small fraction of the time. In addition, visits to the detection volume are fast, lasting only a few microseconds, due to the very small distance that diffusion has to carry the nucleotides. The result is a very low background.

Fluorescent Moieties

In some embodiments, the detectable moiety is a fluorogenic dye. Several classes of fluorogenic dyes and specific compounds are known that are appropriate for particular embodiments of the technology: xanthene derivatives such as fluorescein, rhodamine, Oregon green, eosin, and Texas red; cyanine derivatives such as cyanine, indocarbocyanine, oxacarbocyanine, thiacarbocyanine, and merocyanine; naphthalene derivatives (dansyl and prodan derivatives); coumarin derivatives; oxadiazole derivatives such as pyridyloxazole, nitrobenzoxadiazole, and benzoxadiazole; pyrene derivatives such as cascade blue; oxazine derivatives such as Nile red, Nile blue, cresyl violet, and oxazine 170; acridine derivatives such as proflavin, acridine orange, and acridine yellow; arylmethine derivatives such as auramine, crystal violet, and malachite green; and tetrapyrrole derivatives such as porphin, phthalocyanine, bilirubin. In some embodiments the fluorescent moiety a dye that is xanthene, fluorescein, rhodamine, BODIPY, cyanine, coumarin, pyrene, phthalocyanine, phycobiliprotein, ALEXA FLUOR® 350, ALEXA FLUOR® 405, ALEXA FLUOR® 430, ALEXA FLUOR® 488, ALEXA FLUOR® 514, ALEXA FLUOR® 532, ALEXA FLUOR® 546, ALEXA FLUOR® 555, ALEXA FLUOR® 568, ALEXA FLUOR® 568, ALEXA FLUOR® 594, ALEXA FLUOR® 610, ALEXA FLUOR® 633, ALEXA FLUOR® 647, ALEXA FLUOR® 660, ALEXA FLUOR® 680, ALEXA FLUOR® 700, ALEXA FLUOR® 750, or a squaraine dye.

Furthermore, non-limiting examples of fluorophores include dyes that can be synthesized or obtained commercially (e.g., Operon Biotechnologies, Huntsville, Ala.). A large number of dyes (greater than 50) are available for application in fluorescence excitation applications. These dyes include those from the fluorescein, rhodamine AlexaFluor, Bodipy, Coumarin, and Cyanine dye families. Specific examples of fluorophores include, but are not limited to, FAM, TET, HEX, Cy3, TMR, ROX, Texas red, LC red 640, Cy5, and LC red 705. In some embodiments, dyes with emission maxima from 410 nm (e.g., Cascade Blue) to 775 nm (e.g., Alexa Fluor 750) are available and can be used. Of course, one of ordinary skill in the art will recognize that dyes having emission maxima outside these ranges may be used as well. In some cases, dyes ranging between 500 nm to 700 nm have the advantage of being in the visible spectrum and can be detected using conventional photomultiplier tubes. In some embodiments, the broad range of available dyes allows selection of dye sets that have emission wavelengths that are spread across the detection range. Detection systems capable of distinguishing many dyes are known in the art.

Electrochemically Detectable Moieties

In some embodiments, the nucleotide analogs provided comprise an electrochemical moiety that is an easily oxidizable or reducible species. The electrochemically active moiety can be a number of directly electrochemically active molecules and/or moieties, electrochemical mediators, and/or other labels such as enzymes or other molecules that induce or influence the generation of electronic or electrochemical signals. When attached to a nucleotide analog, the electrochemically active (e.g., electrochemically detectable) moiety identifies the nucleotide base incorporated at the 3' end of the growing strand being synthesized and, thus enables determining the sequence of the strand of DNA or RNA being sequenced. Electrochemically detectable moieties encompassed by the technology include, but are not limited to, an organic redox group, an organometallic group, a metallic nanoparticle, and a quantum dot. Exemplary organic redox groups include, but are not limited to, methylene blue, anthraquinone, and thionine; exemplary organometallic groups include, but are not limited to, ferrocene, ferrocene derivatives, bipyridene complexes of ruthenium, and bipyridene complexes of osmium; exemplary metallic nanoparticles include, but are not limited to, gold and silver; exemplary quantum dots include, but are not limited to, CdS, CdSe, and ZnS. In some embodiments, it is contemplated that the nucleotide analogs comprise a structure as provided in U.S. Pat. Nos. 7,893,227; 7,897,737; 7,964,352; and 8,148,503, with the fluorescent moiety described therein replaced by an electrochemically detectable moiety as described herein or as known in the art.

In some embodiments, the electrochemically detectable moiety comprises a transition-metal such as ruthenium, osmium, iron, rhodium, or copper. Modified nucleic acids comprising these metals are described, e.g., in Angew. Chem., Int. Ed. Engl. 1995, 34, 352-354; Meade, T. J. Metal Ions in Biological Systems; Sigel, A., Sigel, H., Eds.; Marcel Dekker: New York, 1996; pp 32, 453-478; Helv. Chim. Acta 1997, 80, 640-652; J. Am. Chem. Soc. 1998, 120, 2194-2195; J. Am. Chem. Soc. 2000, 122, 6287-6288; Inorg. Chem. 1999, 38, 174-189; Chem. Commun. 1997, 1609-1610; Nucleic Acids Res. 1996, 24, 4273-4280; Chem. Commun. 1996, 555-557; J. Am. Chem. Soc. 1997, 119, 5045-5046; Nature 1996, 382, 731-735; and J. Am. Chem. Soc. 1994. 116, 5981-5982.

An exemplary synthetic method for providing an electrochemically detectable moiety attached to a nucleotide is a reaction for attaching a ferrocene group to the C-5 carbon of thymidine, e.g., as described in Pike et al. (2002) "Metallocene—DNA: Synthesis, Molecular and Electronic Structure and DNA Incorporation of C5-Ferrocenylthymidine Derivatives" *Chem. Eur. J.* 8(13): 2891-2899. Various ferrocenyl thymidine derivatives may be synthesized as follows:

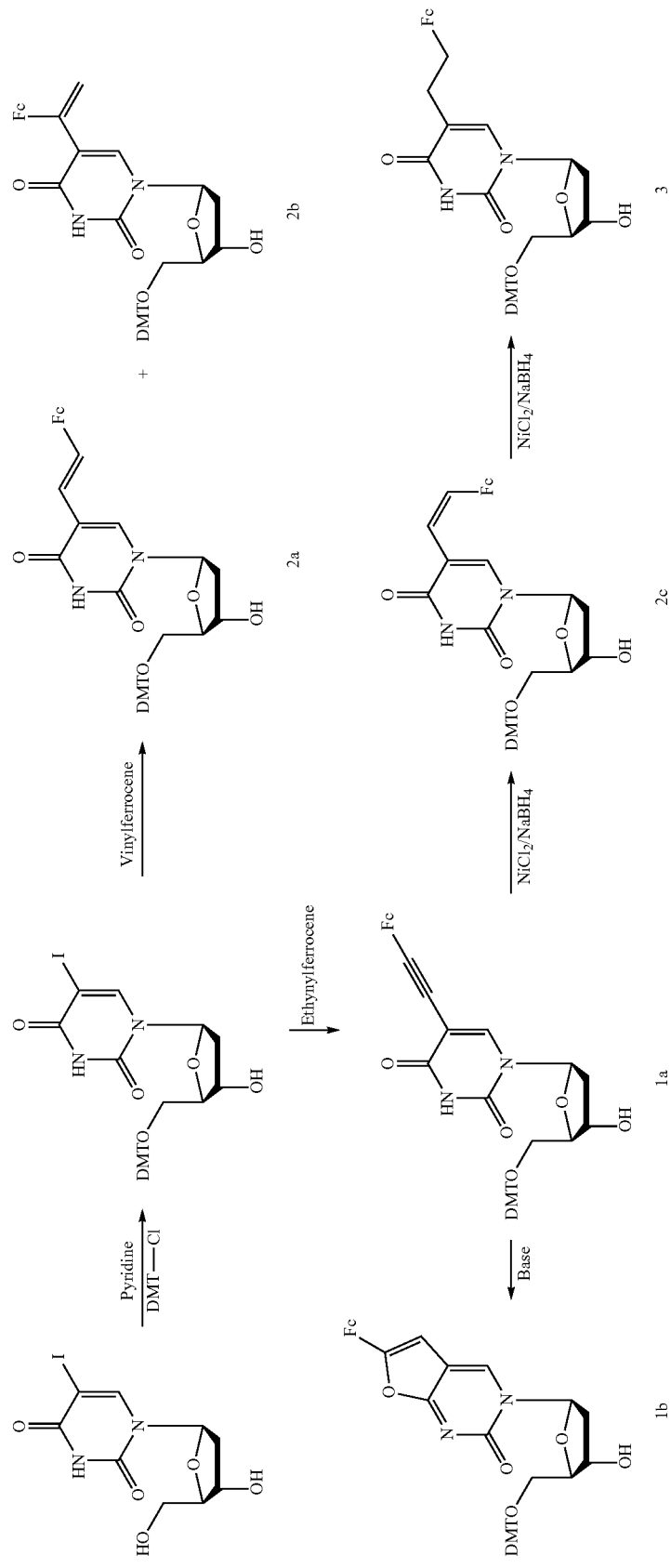

Another exemplary synthetic method for providing an electrochemically detectable moiety attached to a nucleotide is a reaction for attaching an ethynyluracil-modified base to 2-iodoantraquinone, e.g., as described in Gorodetsky et al. (2007) "Coupling into the Base Pair Stack is Necessary for DNA-Mediated Electrochemistry" *Bioconjugate Chem.* 18: 1434-1441.

Another exemplary synthetic method for providing an electrochemically detectable moiety attached to a nucleotide is a reaction for attaching bipyridine complexes of ruthenium, osmium, or other transition metals to nucleotide bases using iodinated nucleotide analog intermediates, e.g., as described in Vrábel et al. (2009) "Base-Modified DNA Labeled by [Ru(bpy)$_3$]$^{2+}$ and [Os(bpy)$_3$]$^{2+}$ Complexes" *Chem. Eur. J.* 15: 1144-1154.

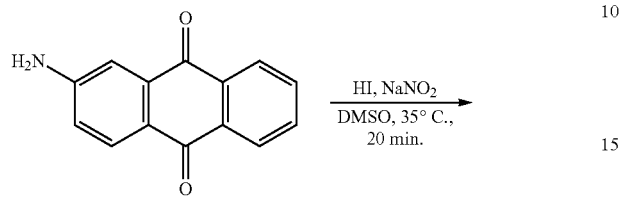

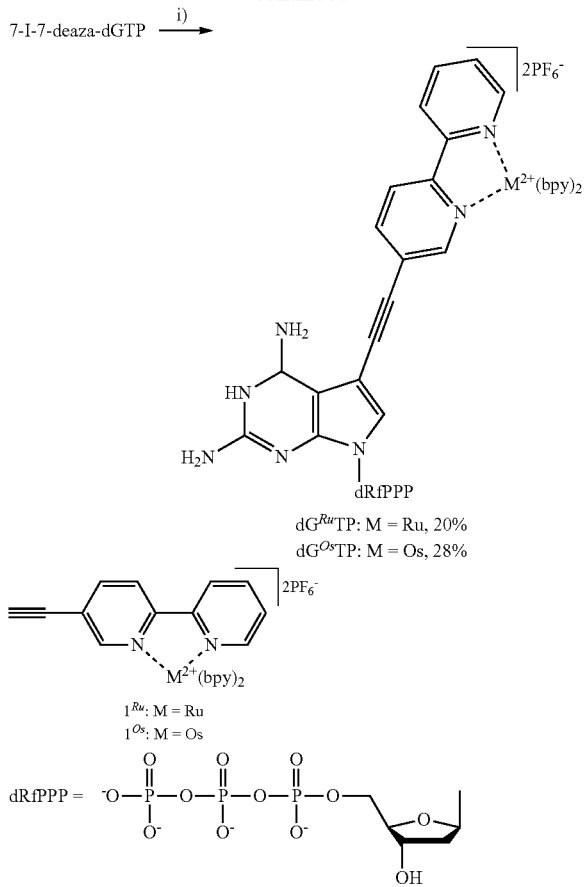

In this scheme, $1^{Ru}$ or $1^{Os}$, Pd(OAc)$_2$, TPPTS, CuI, Et$_3$N, H$_2$O/CH$_3$CN 2:1, 1 hour, 70° C.

Another exemplary synthetic method for providing an electrochemically detectable moiety attached to a nucleotide analog is provided by U.S. Pat. Nos. 7,893,227; 7,897,737; 7,964,352; and 8,148,503, and in Litosh et al (2010) "Improved nucleotide selectivity and termination of 3'-OH unblocked reversible terminators by molecular tuning of 2-nitrobenzyl alkylated HOMedU triphosphates" *Nucleic Acids Res.* 39(6):e39, wherein an electrochemically detectable moiety is substituted for a fluorescently detectable moiety. Chemical intermediates are made using syntheses known in the art such as described by U.S. Pat. Nos. 7,893,227; 7,897,737; 7,964,352; and 8,148,503; in Litosh et al, supra; and as provided by the synthetic schemes described herein. Similar synthetic schemes are used to link redox groups to other parts of the nucleotide, such as the sugar or triphosphate group.

Another exemplary nucleotide comprising an electrochemically detectable moiety is, e.g., a nucleotide comprising a ferrocenyl group linked to the 2'-position of ribose ring. See, e.g., Yu (2001) "2'-Ribose-Ferrocene Oligonucleotides for Electronic Detection of Nucleic Acids" *J. Org. Chem.* 66: 2937-2942, incorporated herein by reference.

Sequencing Methods

The technology relates in some embodiments to methods for sequencing a nucleic acid. In some embodiments, sequencing is performed by the following sequence of events with the exemplary use of a nucleotide analog comprising at least two different photochemical terminating moieties. First, a nucleotide analog comprising an electrochemically or fluorescently detectable terminating moiety (e.g., attached to the nucleotide base) and a second terminating moiety (e.g., attached to the 3' hydroxyl) is oriented in the polymerase active site (e.g., by a polymerase located in the illumination volume of a zero mode waveguide) to be base-paired to a complementary base of the template strand and to be adjacent to the free 3' hydroxyl of the growing synthesized strand. Next, the nucleotide analog is added to the 3' end of a growing strand by the polymerase, e.g., by the enzyme-catalyzed attack of the 3' hydroxyl on the alpha-phosphate of the nucleotide analog. Further extension of the strand by the polymerase is blocked by the 3' terminating group on the incorporated nucleotide analog. The electrochemically or fluorescently detectable moiety on the incorporated nucleotide is queried by an electrochemical detector or by a fluorescence detector (e.g., after excitation by an emission source) to identify the base added to the synthesized strand.

Then, the electrochemically or fluorescently detectable terminating moiety (e.g., attached to the nucleotide base) is removed by exposure (e.g., in the illumination volume of a zero mode waveguide) to a wavelength of light that cleaves the electrochemically or fluorescently detectable terminating moiety from the nucleotide analog. While the electrochemically or fluorescently detectable terminating moiety has been released, further extension of the strand by the polymerase remains blocked by the 3' terminating group (second terminating moiety) on the incorporated nucleotide analog. Then, the second terminating moiety is removed by exposure (e.g., in the illumination volume of a zero mode waveguide) to a wavelength of light that cleaves the second terminating moiety from the nucleotide analog. In some embodiments, the wavelength of light that cleaves the electrochemically or fluorescently detectable terminating moiety is different than the wavelength of light that cleaves the second terminating moiety, e.g., blocking the 3' hydroxyl. After the second terminating moiety is released, the 3' hydroxyl of the growing strand is free for further polymerization: the next base is incorporated to continue another cycle, e.g., a nucleotide analog is oriented in the polymerase active site, the nucleotide analog is added to the 3' end of the growing strand by the polymerase, the nucleotide analog is queried to identify the base added, and the nucleotide analog is deprotected.

Some embodiments relate to parallel (e.g., massively parallel) sequencing. For example, in some embodiments all sequencing reactions are exposed to light in parallel to deprotect the nucleotide analogs in parallel. Identification of the base incorporated is performed using electrochemical detection of the electrochemically detectable moiety (e.g., that provides a "signature" of each base) before it is cleaved.

In some embodiments sequencing is performed by the following sequence of events with the exemplary use of a nucleotide comprising one photochemical terminating moiety. First, a nucleotide analog comprising an electrochemically detectable terminating moiety (e.g., attached to the nucleotide base) is oriented in the polymerase active site (e.g., by a polymerase located in the illumination volume of a zero mode waveguide) to be base-paired to a complementary base of the template strand and to be adjacent to the free 3' hydroxyl of the growing synthesized strand. Next, the nucleotide analog is added to the 3' end of a growing strand by the polymerase, e.g., by the enzyme-catalyzed attack of the 3' hydroxyl on the alpha-phosphate of the nucleotide analog. Further extension of the strand by the polymerase is blocked by the electrochemically detectable terminating moiety of incorporated nucleotide analog, e.g., by steric hindrance of the catalysis, deformation of the active site constituents, etc. The electrochemically detectable moiety on the incorporated nucleotide is queried by an electrochemical detector to identify the base added to the synthesized strand.

Then, the electrochemically detectable terminating moiety (e.g., attached to the nucleotide base) is removed by exposure (e.g., in the illumination volume of a zero mode waveguide) to a wavelength of light that cleaves the electrochemically detectable terminating moiety from the nucleotide analog. After the electrochemically detectable terminating moiety is released, the 3' hydroxyl of the growing strand is free for further polymerization: the next base is incorporated to continue another cycle, e.g., a nucleotide analog is oriented in the polymerase active site, the nucleotide analog is added to the 3' end of the growing strand by the polymerase, the nucleotide analog is queried to identify the base added, and the nucleotide analog is deprotected.

Accordingly, in some embodiments, the technology provides that nucleotides on the end of the chain are 3' protected so they cannot react with the 5' triphosphate from new nucleotides coming into the active site until after deblocking the 3' end (either by removing a terminating moiety from the 3' hydroxyl or by removing steric hindrance to polymerization). Thus, one can read all or substantially all of the fluorescence or electrochemical signal without the problems associated with reincorporation and reading of the next base. In embodiments related to electrochemical detection based reagents, such reagents are developed for sequencing using photochemical deprotection using a single photochemical deprotection group and an electrochemically active element serving for detection. This approach improves existing technologies (e.g., as provided by the LaserGen chemistry) and thus finds use in sequencing by synthesis applications having increased accuracy lower cost by including these approaches on low cost optical systems such as zero mode waveguide-based systems and the like.

Nucleic Acid Sequencing Platforms

In some embodiments of the technology, nucleic acid sequence data are generated. Various embodiments of nucleic acid sequencing platforms (e.g., a nucleic acid sequencer) include components as described below. According to various embodiments, a sequencing instrument includes a fluidic delivery and control unit, a sample processing unit, a signal detection unit, and a data acquisition, analysis and control unit. Various embodiments of the instrument provide for automated sequencing that is used to gather sequence information from a plurality of sequences in parallel and/or substantially simultaneously.

In some embodiments, the fluidics delivery and control unit includes a reagent delivery system. The reagent delivery system includes a reagent reservoir for the storage of various reagents. The reagents can include RNA-based primers, forward/reverse DNA primers, nucleotide mixtures (e.g., compositions comprising nucleotide analogs as provided herein) for sequencing-by-synthesis, buffers, wash reagents, blocking reagents, stripping reagents, and the like. Additionally, the reagent delivery system can include a pipetting system or a continuous flow system that connects the sample processing unit with the reagent reservoir.

In some embodiments, the sample processing unit includes a sample chamber, such as flow cell, a substrate, a micro-array, a multi-well tray, or the like. The sample processing unit can include multiple lanes, multiple channels, multiple wells, or other means of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber. In some embodiments, the signal detection unit can include an imaging or detection sensor. For example, the imaging or detection sensor (e.g., a fluorescence detector or an electrical detector) can include a CCD, a CMOS, an ion sensor, such as an ion sensitive layer overlying a CMOS, a current detector, or the like. The signal detection unit can include an excitation system to cause a probe, such as a fluorescent dye, to emit a signal. The detection system can include an illumination source, such as arc lamp, a laser, a light emitting diode (LED), or the like. In particular embodiments, the signal detection unit includes optics for the transmission of light from an illumination source to the sample or from the sample to the imaging or detection sensor. Alternatively, the signal detection unit may not include an illumination source, such as for example, when a signal is produced spontaneously as a result of a sequencing reaction. For example, a signal can be produced by the interaction of a released moiety, such as a released ion interacting with an ion sensitive layer, or a pyrophosphate reacting with an enzyme or other catalyst to produce a chemiluminescent signal. In another example, changes in an electrical current, voltage, or resistance are detected without the need for an illumination source.

In some embodiments, a data acquisition analysis and control unit monitors various system parameters. The system parameters can include temperature of various portions of the instrument, such as sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of the instruments and systems are used to practice sequencing methods such as sequencing by synthesis, single molecule methods, and other sequencing techniques. Sequencing by synthesis can include the incorporation of dye labeled nucleotides, chain termination, ion/proton sequencing, pyrophosphate sequencing, or the like. Single molecule techniques can include staggered sequencing, where the sequencing reactions is paused to determine the identity of the incorporated nucleotide.

In some embodiments, the sequencing instrument determines the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In some embodiments, the nucleic acid can include or be derived from a fragment library, a mate pair library, a ChIP fragment, or the like. In particular embodiments, the sequencing instrument can obtain the sequence information from a single nucleic acid molecule or from a group of substantially identical nucleic acid molecules.

In some embodiments, the sequencing instrument can output nucleic acid sequencing read data in a variety of different output data file types/formats, including, but not limited to: *.txt, *.fasta, *.csfasta, *seq.txt, *qseq.txt, *.fastq, *.sff, *prb.txt, *.sms, *srs, and/or *.qv.

Nucleic Acid Analysis

In some embodiments, a computer-based analysis program is used to translate the raw data generated by the detection assay (e.g., sequencing reads) into data of predictive value for an end user (e.g., medical personnel). The user can access the predictive data using any suitable means.

Thus, in some preferred embodiments, the present technology provides the further benefit that the user, who is not likely to be trained in genetics or molecular biology, need not understand the raw data. The data is presented directly to the end user in its most useful form. The user is then able to immediately utilize the information to determine useful information (e.g., in medical diagnostics, research, or screening).

Some embodiments provide a system for reconstructing a nucleic acid sequence. The system can include a nucleic acid sequencer, a sample sequence data storage, a reference sequence data storage, and an analytics computing device/server/node. In some embodiments, the analytics computing device/server/node can be a workstation, mainframe computer, personal computer, mobile device, etc. The nucleic acid sequencer can be configured to analyze (e.g., interrogate) a nucleic acid fragment (e.g., single fragment, mate-pair fragment, paired-end fragment, etc.) utilizing all available varieties of techniques, platforms or technologies to obtain nucleic acid sequence information, in particular the methods as described herein using compositions provided herein. In some embodiments, the nucleic acid sequencer is in communications with the sample sequence data storage either directly via a data cable (e.g., serial cable, direct cable connection, etc.) or bus linkage or, alternatively, through a network connection (e.g., Internet, LAN, WAN, VPN, etc.). In some embodiments, the network connection can be a "hardwired" physical connection. For example, the nucleic acid sequencer can be communicatively connected (via Category 5 (CAT5), fiber optic or equivalent cabling) to a data server that is communicatively connected (via CAT5, fiber optic, or equivalent cabling) through the Internet and to the sample sequence data storage. In some embodiments, the network connection is a wireless network connection (e.g., Wi-Fi, WLAN, etc.), for example, utilizing an 802.11 a/b/g/n or equivalent transmission format. In practice, the network connection utilized is dependent upon the particular requirements of the system. In some embodiments, the sample sequence data storage is an integrated part of the nucleic acid sequencer.

In some embodiments, the sample sequence data storage is any database storage device, system, or implementation (e.g., data storage partition, etc.) that is configured to organize and store nucleic acid sequence read data generated by nucleic acid sequencer such that the data can be searched and retrieved manually (e.g., by a database administrator or client operator) or automatically by way of a computer program, application, or software script. In some embodiments, the reference data storage can be any database device, storage system, or implementation (e.g., data storage partition, etc.) that is configured to organize and store reference sequences (e.g., whole or partial genome, whole or partial exome, SNP, gen, etc.) such that the data can be searched and retrieved manually (e.g., by a database administrator or client operator) or automatically by way of a computer program, application, and/or software script. In some embodiments, the sample nucleic acid sequencing read data can be stored on the sample sequence data storage and/or the reference data storage in a variety of different data file types/formats, including, but not limited to: *.txt, *.fasta, *.csfasta, *seq.txt, *qseq.txt, *.fastq, *.sff, *prb.txt, *.sms, *srs and/or *.qv.

In some embodiments, the sample sequence data storage and the reference data storage are independent standalone devices/systems or implemented on different devices. In some embodiments, the sample sequence data storage and the reference data storage are implemented on the same device/system. In some embodiments, the sample sequence data storage and/or the reference data storage can be implemented on the analytics computing device/server/node. The analytics computing device/server/node can be in communications with the sample sequence data storage and the reference data storage either directly via a data cable (e.g., serial cable, direct cable connection, etc.) or bus linkage or, alternatively, through a network connection (e.g., Internet, LAN, WAN, VPN, etc.). In some embodiments, analytics computing device/server/node can host a reference mapping engine, a de novo mapping module, and/or a tertiary analysis engine. In some embodiments, the reference mapping engine can be configured to obtain sample nucleic acid sequence reads from the sample data storage and map them against one or more reference sequences obtained from the reference data storage to assemble the reads into a sequence that is similar but not necessarily identical to the reference sequence using all varieties of reference mapping/alignment techniques and methods. The reassembled sequence can then be further analyzed by one or more optional tertiary analysis engines to identify differences in the genetic makeup (genotype), gene expression or epigenetic status of individuals that can result in large differences in physical characteristics (phenotype). For example, in some embodiments, the tertiary analysis engine can be configured to identify various genomic variants (in the assembled sequence) due to mutations, recombination/crossover or genetic drift. Examples of types of genomic variants include, but are not limited to: single nucleotide polymorphisms (SNPs), copy number variations (CNVs), insertions/deletions (Indels), inversions, etc. The optional de novo mapping module can be configured to assemble sample nucleic acid sequence reads from the sample data storage into new and previously unknown sequences. It should be understood, however, that the various engines and modules hosted on the analytics computing device/server/node can be combined or collapsed into a single engine or module, depending on the requirements of the particular application or system architecture. Moreover, in some embodiments, the analytics computing device/server/node can host additional engines or modules as needed by the particular application or system architecture.

In some embodiments, the mapping and/or tertiary analysis engines are configured to process the nucleic acid and/or reference sequence reads in color space. In some embodiments, the mapping and/or tertiary analysis engines are configured to process the nucleic acid and/or reference sequence reads in base space. It should be understood, however, that the mapping and/or tertiary analysis engines disclosed herein can process or analyze nucleic acid sequence data in any schema or format as long as the schema or format can convey the base identity and position of the nucleic acid sequence.

In some embodiments, the sample nucleic acid sequencing read and referenced sequence data can be supplied to the analytics computing device/server/node in a variety of different input data file types/formats, including, but not limited to: *.txt, *.fasta, *.csfasta, *seq.txt, *qseq.txt, *.fastq, *.sff, *prb.txt, *.sms, *srs and/or *.qv.

Furthermore, a client terminal can be a thin client or thick client computing device. In some embodiments, client terminal can have a web browser that can be used to control the operation of the reference mapping engine, the de novo mapping module and/or the tertiary analysis engine. That is, the client terminal can access the reference mapping engine, the de novo mapping module and/or the tertiary analysis engine using a browser to control their function. For example, the client terminal can be used to configure the operating parameters (e.g., mismatch constraint, quality value thresholds, etc.) of the various engines, depending on the requirements of the particular application. Similarly, client terminal can also display the results of the analysis performed by the reference mapping engine, the de novo mapping module and/or the tertiary analysis engine.

The present technology also encompasses any method capable of receiving, processing, and transmitting the information to and from laboratories conducting the assays, information provides, medical personal, and subjects.

Although the disclosure herein refers to certain illustrated embodiments, it is to be understood that these embodiments are presented by way of example and not by way of limitation.

EXAMPLES

1. Synthesis of (S)-t-butyl-5-methoxy-2-nitrobenzyl Alcohol Intermediate

Scheme S4. Synthesis of (R/S)-1-(5-methoxy-2-nitrophenyl)-2,2-dimethyl-1-propanol and (S)-1-(5-methoxy-2-nitrophenyl)-2,2-dimethyl-1-propanol. Reagents and conditions: (i) PhMgCl, anhydrous THF, minus 40° C.; (CH$_3$)$_3$CCHO, minus 40° C. to room temperature, 88%; (ii) (1S)-camphanic acid chloride, DMAP, CH$_2$Cl$_2$, room temperature; (iii) fractional crystallization from ethyl acetate/hexane, 43%; (iv) K$_2$CO$_3$, MeOH, reflux, 99%.

(R/S)-1-(5-Methoxy-2-nitrophenyl)-2,2-dimethyl-1-propanol and (S)-1-(5-methoxy-2-nitro-phenyl)-2,2-dimethyl-1-propanol

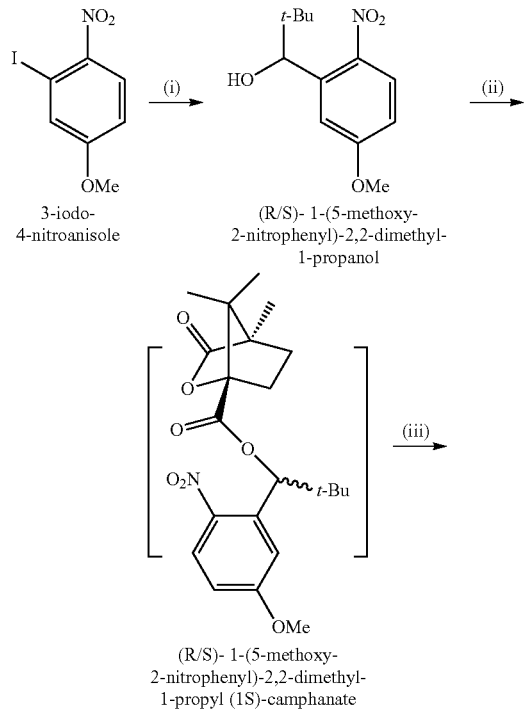

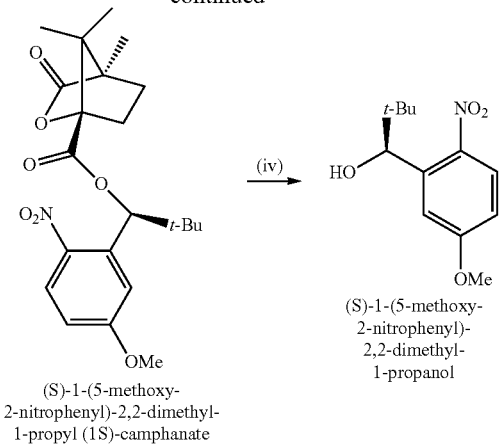

To a solution of 3-iodo-4-nitroanisole (2.79 g, 10.0 mmol) in anhydrous THF (10 mL) at minus 40° C. under a nitrogen atmosphere, phenylmagnesium chloride (2 M in THF, 4.2 mL, 8.3 mmol) was added dropwise at a rate such that the temperature would not exceed minus 35° C. Upon completion of the addition, the mixture was stirred at minus 40° C. for two hours, followed by addition of trimethylacetaldehyde (1.1 mL, 10 mmol). The mixture was stirred at minus 40° C. for two hours and then at room temperature for another one hour. The reaction was then quenched with brine (100 mL), and the mixture was extracted with CH$_2$Cl$_2$ (40 mL) three times. The combined organic phase was dried over Na$_2$SO$_4$, concentrated in vacuo, and the residue was purified by silica gel column chromatography to yield racemic (R/S)-1-(5-methoxy-2-nitrophenyl)-2,2-dimethyl-1-propanol (1.76 g, 88%).

1H NMR (400 MHz, CDCl$_3$): δ 7.89 (d, 1H, J=9.2 Hz, Ph-H), 7.27 (d, 1H, J=2.8 Hz, Ph-H), 6.84 (dd, 1H, J=8.8 and 2.8 Hz, Ph-H), 5.62 (d, 1H, J=4.0 Hz, PhCH), 3.89 (s, 3H, OCH$_3$), 2.08 (d, 1H, J=4.0 Hz, OH), 0.89 (s, 9H, C(CH$_3$)$_3$).

To a solution of racemic (R/S)-1-(5-methoxy-2-nitrophenyl)-2,2-dimethyl-1-propanol (1.75 g, 7.3 mmol) and DMAP (2.92 g, 23.9 mmol) in anhydrous CH$_2$Cl$_2$ (10 mL), (1S)-camphanic chloride (2.6 g, 12 mmol) was added, and the mixture was stirred overnight at room temperature under a nitrogen atmosphere. The reaction mixture was diluted with CH$_2$Cl$_2$ (50 mL) and washed with saturated NaHCO$_3$ solution (50 mL). The organic phase was dried over Na$_2$SO$_4$, concentrated in vacuo, and the residue was purified by silica gel column chromatography to yield (R/S)-1-(5-methoxy-2-nitrophenyl)-2,2-dimethyl-1-propyl (1S)-camphanate (2.5 g, 85%, 1:1 mixture of diastereomers). The camphanate was dissolved in ethyl acetate (30 mL) followed by slow addition of hexane (120 mL) with stirring. Needle crystals formed gradually from the solution over a two-hour period. The crystals were collected by filtration to yield pure single diastereomer (S)-1-(5-methoxy-2-nitrophenyl)-2,2-dimethyl-1-propyl (1S)-camphanate. The filtrate was concentrated in vacuo, and the crystallization process was repeated twice to provide additional (S)-1-(5-methoxy-2-nitrophenyl)-2,2-dimethyl-1-propyl (1S)-camphanate (total 1.08 g, 43%).

1H NMR (400 MHz, CDCl$_3$): δ 8.04 (d, 1H, J=9.2 Hz, Ph-H), 7.27 (d, 1H, J=2.8 Hz, Ph-H), 6.88 (dd, 1H, J=2.8 and 8.8 Hz, Ph-H), 6.81 (3, 1 H, Ph-CH), 3.87 (s, 3H, OCH$_3$), 2.36 (m, 1H, CH), 1.92 (m, 2H, CH$_2$), 1.66 (m, 1H, CH), 1.12 (s, 3H, CH$_3$), 1.06 (s, 3H, CH$_3$), 1.02 (s, 3H, CH$_3$), 0.95 (s, 9H, C(CH$_3$)$_3$).

2. Synthesis of 5-bromomethyl-2'-deoxyuridine Analog

Scheme S5. Synthesis of 5-(2-nitrobenzyloxy)methyl-dUTP analogs. Reagents and conditions: (i) TBSCl, imidazole, anhydrous DMF, room temperature, 16 hr, 95%; (ii) Boc₂O, DMAP, anhydrous DMF, room temperature, 16 hr, 78%; (iii) N-bromosuccinimide, benzoyl peroxide, CCl₄, reflux, one hr, 43%;

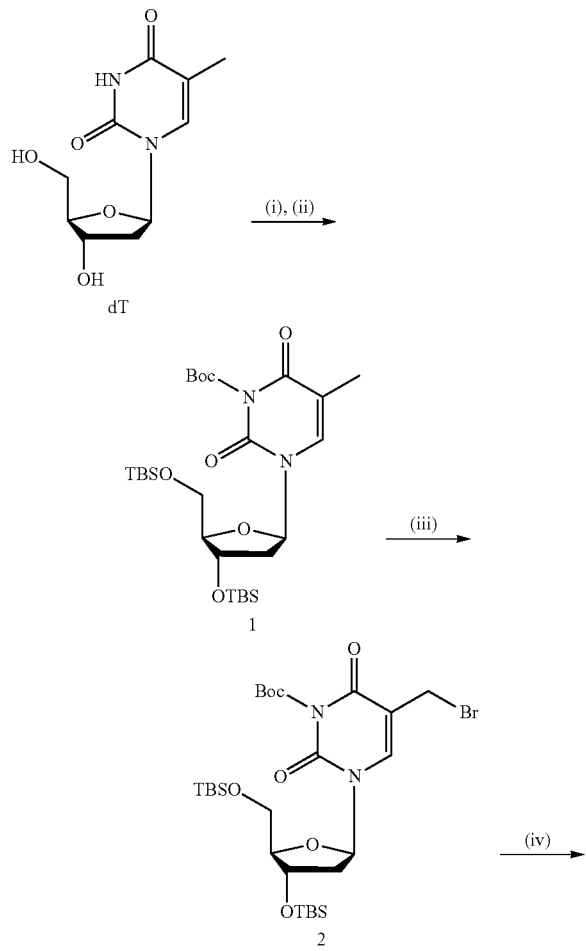

3',5'-O-Bis-tert-butyldimethylsilyl-$N_3$-tert-butyloxycarbonyl-thymidine (1). To a solution of thymidine (5.00 g, 20.64 mmol) and imidazole (9.0 g, 132.1 mmol) in anhydrous DMF (11 mL), a solution of TBSCl (9.96 g, 66.05 mmol) in anhydrous DMF (11 mL) was added dropwise, and the mixture was stirred at room temperature for 16 hr under a nitrogen atmosphere. Solvent was removed in vacuo, and the residue was purified by silica gel column chromatography to yield 3',5'-O-bis-tert-butyldimethylsilyl-thymidine (9.23 g, 95%) as a white solid.

1H NMR (400 MHz, CDCl₃): δ 8.51 (br s, 1H, NH), 7.48 (d, 1H, J=1.2 Hz, H-6), 6.34 (dd, 1H, J=5.8 and 8.0 Hz, H-1'), 4.41 (m, 1H, H-3'), 3.93 (m, 1H, H-4'), 3.87 (dd, 1H, J=2.6 and 11.4 Hz, H-5'a), 3.76 (dd, 1H, J=2.6 and 11.4 Hz, H-5'b), 2.17 (m, 1H, H-2'a), 2.01 (m, 1H, H-2'b), 1.92 (d, 3H, J=1.2 Hz, CH₃), 0.93 (s, 9H, (CH₃)₃CSi), 0.88 (s, 9H, (CH₃)₃CSi), 0.11 (s, 6H, (CH₃)₂Si), 0.08 (s, 6H, (CH₃)₂Si).

To a solution of compound 3',5'-O-bis-tert-butyldimethylsilyl-thymidine (2.43 g, 5.15 mmol) and DMAP (1.39 g, 11.34 mmol) in anhydrous DMF (45 mL), a solution of di-tert-butyldicarbonate (2.47 g, 11.34 mmol) in anhydrous DMF (9 mL) was added dropwise. The mixture was stirred at room temperature for 16 hr under a nitrogen atmosphere. The mixture was then concentrated in vacuo, and the residue was dissolved in CH₂Cl₂ (80 mL), washed with saturated NH₄Cl solution (10 mL), dried over Na₂SO₄, and concentrated in vacuo. The residue was purified by silica gel column chromatography to yield 3',5'-O-bis-tert-butyldimethylsilyl-$N_3$-tert-butyloxycarbonyl-thymidine 1 (2.30 g, 78%) as a white solid.

1H NMR (400 MHz, CDCl₃): δ 7.50 (d, 1H, J=1.2 Hz, H-6), 6.34 (dd, 1H, J=5.8 and 8.0 Hz, H-1'), 4.42 (m, 1H, H-3'), 3.95 (m, 1H, H-4'), 3.87 (dd, 1H, J=2.5 and 11.4 Hz, H-5'a), 3.76 (dd, 1H, J=2.5 and 11.4 Hz, H-5'b), 2.17 (m, 1H, H-2'a), 2.01 (m, 1H, H-2'b), 1.92 (d, 3H, J=1.2 Hz, CH₃), 1.60 (s, 9H, (CH₃)₃), 0.93 (s, 9H, (CH₃)₃CSi), 0.88 (s, 9H, (CH₃)₃CSi), 0.11 (s, 6H, (CH₃)₂Si), 0.08 (s, 6H, (CH₃)₂Si).

3',5'-Bis-O-tert-butyldimethylsilyl-$N_3$-tert-butyloxycarbonyl-5-bromomethyl-2'-deoxyuridine (2). A solution of compound 1 (570 mg, 1.00 mmol), N-bromosuccinimide (0.37 g, 2.10 mmol), and benzoyl peroxide (10 mg, 75% aqueous solution) in CCl₄ (10 mL) was heated at reflux for one hr (7). The mixture was filtered, and the filtrate was concentrated in vacuo and purified by silica gel column chromatography to yield 3',5'-bis-O-tert-butyldimethylsilyl-$N_3$-tertbutyloxycarbonyl-5-bromomethyl-2'-deoxyuridine 2 (281 mg, 43%) as a yellow solid.

1H NMR (400 MHz, CDCl₃): δ 7.89 (s, 1H, H-6), 6.27 (dd, 1H, J=5.8 and 8.0 Hz, H-1'), 4.38 (m, 1H, H-3'), 4.27 (d, 1H, J=10.6 Hz, CH₂Br), 4.20 (d, 1H, J=10.6 Hz, CH₂Br), 3.98 (m, 1H, H-4'), 3.88 (dd, 1H, J=2.5 and 11.4 Hz, H-5'b), 3.77 (dd, 1H, J=2.6 and 11.4 Hz, H-5'a), 2.33 (m, 1H, H-2'a), 2.01 (m, 1H, H-2'b), 1.61 (s, 9H, (CH₃)₃), 0.95 (s, 9H, (CH₃)₃CSi), 0.89 (s, 9H, (CH₃)₃CSi), 0.14 (s, 6H, (CH₃)₂Si), 0.07 (s, 6H, (CH₃)₂Si); 13C NMR (100 MHz, CDCl₃): δ 159.21 (C), 147.99 (C), 147.32 (C), 138.46 (CH), 111.30 (C), 88.34 (CH), 87.22 (C), 86.00 (CH), 72.28 (CH), 63.04 (CH₂), 41.93 (CH₂), 27.42 (CH₃), 25.99 (CH₃), 25.71 (CH₃), 25.65 (CH₃), 24.91 (CH₂), 18.47 (C), 17.97 (C), −3.58 (CH₃), −4.65 (CH₃), −4.86 (CH₃), −5.32 (CH₃).

3. Synthesis of 5-HOMe-2'-deoxyuridine Triphosphate Analog

Scheme S19. Synthesis of 5-[(S)-1-(5-methoxy-2-nitrophenyl)-2,2-dimethyl-propyloxy]methyl-2¢-deoxyuridine-S¢-triphosphate. Reagents and conditions: (i) (S)-1-(5-methoxy-2-nitrophenyl)-2,3-dimethyl-1-propanol, 110° C.; (ii) NH₄F, MeOH, 50° C., 56% for two steps; (iii) POCl₃, proton sponge, (MeO)₃PO, 0° C.; (n-Bu₃NH)₂H₂P₂O₇, n-Bu₃N, DMF; 1 M HNEt₃HCO₃.

5-[(S)-1-(5-Methoxy-2-nitrophenyl)-2,2-dimethyl-propyloxy]methyl-2'-deoxyuridine-5'-triphpsphate

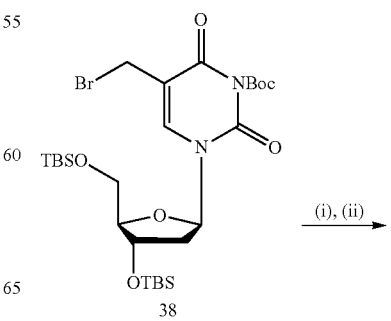

-continued

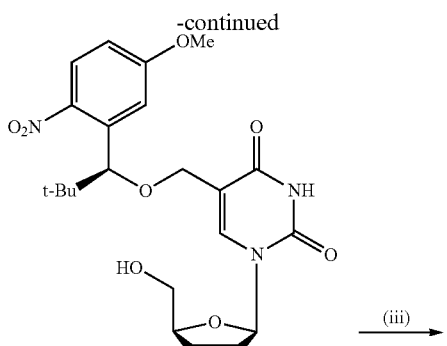

39

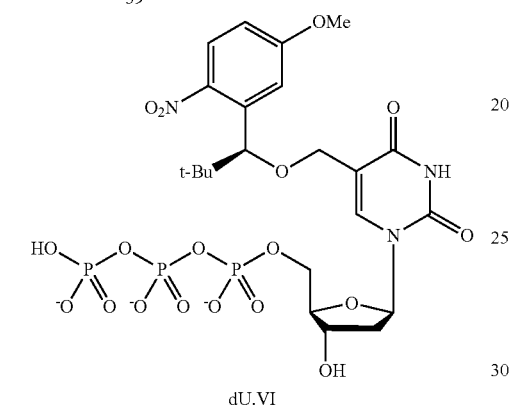

dU.VI

Compound 38 (315 mg, 0.49 mmol) and (S)-1-(5-methoxy-2-nitrophenyl)-2,2-dimethyl-1-propanol (490 mg, 2.1 mmol) were heated at 110° C. for 45 min under a nitrogen atmosphere. The mixture was cooled down to room temperature, dissolved in MeOH (10 mL), and followed by addition of $NH_4F$ (400 mg, 11 mmol). The mixture was stirred at 50° C. for 12 hours, concentrated in vacuo, dissolved in $CH_2Cl_2$ (50 mL), and washed with brine (50 mL). The organic phase was dried over $Na_2SO_4$, concentrated in vacuo, and the residue was purified by silica gel chromatography to yield 5-[(S)-1-(5-methoxy-2-nitrophenyl)-2,2-dimethyl-propyloxy]methyl-2'-deoxyuridine 39 (130 mg, 56%).

1H NMR (400 MHz, $CDCl_3$): δ 9.14 (br s, 1H, NH), 7.90 (d, 1H, J=9.2 Hz, Ph-H), 7.67 (s, 1H, H-6), 7.17 (d, 1H, J=2.8 Hz, Ph-H), 6.84 (dd, 1H, J=9.2 and 2.8 Hz, Ph-H), 6.18 (t, 1H, J=6.4 Hz, H-1'), 5.22 (s, 1H, Ph-CH), 4.56 (m, 1H, H-3'), 4.24 (d, 1H, J=12.4 Hz, 5-CH2a), 4.15 (d, 1H, J=12.4 Hz, 5-CH2b), 4.00 (m, 1H, H-4'), 3.90 (m, 1H, H-5'a), 3.88 (s, 3H, $OCH_3$), 3.81 (m, 1H, H-5'b), 2.35 (m, 2H, H-2), 0.83 (s, 9H, $C(CH_3)_3$).

Compound 39 (30 mg, 0.065 mmol) was phosphorylated with $POCl_3$ (9 μL, 0.097 mmol) and proton sponge (28 mg, 0.13 mmol) in trimethylphosphate (0.35 mL) at 0° C. for one hour under a nitrogen atmosphere. A solution of tri-n-butylammonium pyrophosphate (147 mg, 0.32 mmol) and tri-n-butylamine (64 μL) in anhydrous DMF (0.64 mL) was added. After 10 min of stirring, triethylammonium bicarbonate buffer (0.1 M, pH 7.5; 10 mL) was added. The reaction was stirred at room temperature for one hour and then concentrated in vacuo. The residue was dissolved in 20% aqueous acetonitrile (10 mL), filtered, and purified by anion exchange chromatography. The fractions containing triphosphate were combined and lyophilized to yield 5-[(S)-1-(5-methoxy-2-nitrophenyl)-2,2-dimethyl-propyl]oxymethyl-2'-deoxyuridine-5'-triphosphate dU.VI, which was further purified using RP-HPLC.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A system for sequencing a nucleic acid, comprising:
   a) a first nucleotide analog comprising an adenine nucleotide;
   b) a second nucleotide analog comprising a cytosine nucleotide;
   c) a third nucleotide analog comprising a guanine nucleotide; and
   d) a fourth nucleotide analog comprising a thymine or a uracil nucleotide:
   wherein one or more of said first nucleotide analog, said second nucleotide analog, said third nucleotide analog and said fourth nucleotide analog comprises:
      i) a phosphate moiety;
      ii) a base;
      iii) a sugar;
      iv) a first photocleavable terminating moiety attached to said nucleotide analog by a first photocleavable linker, wherein said photocleavable terminating moiety is electrochemically detectable by accepting or donating at least one electron during an electrochemical reaction; and
      v) a second photocleavable terminating moiety attached to said nucleotide analog by a second photocleavable linker.

2. The system of claim 1, wherein said first nucleotide analog comprises a first electrochemically detectable moiety or a first fluorescently detectable moiety, said second nucleotide analog comprises a second electrochemically detectable moiety or a second fluorescently detectable moiety, said third nucleotide analog comprises a third electrochemically detectable moiety or a third fluorescently detectable moiety, and said fourth nucleotide analog comprises a fourth electrochemically detectable moiety or a fourth fluorescently detectable moiety.

3. The system of claim 1, wherein said electrochemically detectable, photocleavable terminating moiety is attached to said phosphate moiety, said base or said sugar of said nucleotide analog.

4. The system of claim 1, wherein said phosphate moiety is a triphosphate moiety, a diphosphate moiety or a monophosphate moiety.

5. The system of claim 1, wherein said electrochemically detectable, photocleavable terminating moiety is a group imparting polymerase termination properties to said nucleotide analog.

6. The system of claim 1, further comprising a substrate comprising a zero mode waveguide.

7. The system of claim 1, further comprising an electrical detection element and/or a fluorescence detection element.

8. The system of claim 1, further comprising a polymerase.

9. The system of claim 1, further comprising an illumination source.

10. The system of claim 1, further comprising a nucleic acid sequencer.

11. The system of claim 1, further comprising a sample sequence data storage.

12. The system of claim 1, further comprising a reference sequence data storage.

13. The system of claim 1, further comprising an analytics computing device, server or node.

14. The system of claim 1, further comprising a software component.

15. The system of claim 1, further comprising a sample processing unit.

16. The system of claim 1, further comprising a reagent delivery system.

17. The system of claim 1, further comprising a reagent reservoir.

18. The system of claim 1, further comprising a manipulator, a stepper motor and/or a pump.

\* \* \* \* \*